United States Patent
Jaroch et al.

(10) Patent No.: US 6,579,883 B1
(45) Date of Patent: Jun. 17, 2003

(54) FLUORINATED 3,4-DIHYDROQUINOLINE DERIVATIVES USED AS NOS INHIBITORS

(75) Inventors: Stefan Jaroch, Berlin (DE); Hartmut Rehwinkel, Berlin (DE); Peter Hölscher, Berlin (DE); Detlev Sülzle, Berlin (DE); Margrit Hillmann, Berlin (DE); Gerardine Anne Burton, Berlin (DE); Fiona Macdougall McDonald, Berlin (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/831,514
(22) PCT Filed: Nov. 10, 1999
(86) PCT No.: PCT/EP99/08519
§ 371 (c)(1), (2), (4) Date: May 10, 2001
(87) PCT Pub. No.: WO00/29381
PCT Pub. Date: May 25, 2000

(30) Foreign Application Priority Data

Nov. 13, 1998 (DE) .......................... 198 54 042

(51) Int. Cl.[7] ................... A61K 31/473; A61K 31/435; C07D 221/16; A61P 9/00; A61P 29/00
(52) U.S. Cl. .................. 514/290; 514/289; 514/291; 514/232.8; 544/126; 546/74; 546/79; 546/80; 546/89; 546/93; 546/101
(58) Field of Search ............... 546/79, 80, 89, 546/93, 101, 74; 544/126; 514/232.8, 290, 291, 289

(56) References Cited

FOREIGN PATENT DOCUMENTS

| CA | 2340990 | 3/2000 |
|---|---|---|
| WO | 96 14844 | 5/1996 |
| WO | 9618616 | 6/1996 |
| WO | 9709982 | 3/1997 |
| WO | 9736871 | 10/1997 |

OTHER PUBLICATIONS

Weber et al. "Substituted 2–Iminipiperidines as inhibitors of Human Oxide Synthase isoforms" J. Med. Chem. 1998,41, pp. 96–101.
Abstract for HU010415.

*Primary Examiner*—Evelyn Mei Huang
(74) *Attorney, Agent, or Firm*—Millen, White, Zelano and Branigan, P.C.

(57) ABSTRACT

The invention relates to compounds of formula (I), to a method for producing them and to their use in medicaments as NOS inhibitors.

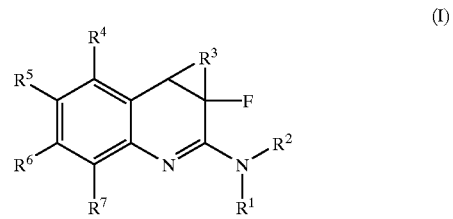

14 Claims, No Drawings

FLUORINATED 3,4-DIHYDROQUINOLINE DERIVATIVES USED AS NOS INHIBITORS

This application is a 371 of PCT/EP99/08519, filed on Nov. 10, 1999.

The invention relates to fluorinated 3,4-dihydroquinoline derivatives, a process for their production and their use in pharmaceutical agents.

In human cells, there exist at least three forms of nitrogen monoxide synthases, which convert arginine into nitrogen monoxide (NO) and citrulline. Two constitutive NO-synthases (NOS) were identified that are present as calcium/calmodulin-dependent enzymes in the brain (ncNOS or NOS 1) or in the endothelium (ecNOS or NOS 3). Another isoform is the inducible NOS (iNOS or NOS 2), which is a virtually $Ca^{++}$-independent enzyme and is induced after activation of different cells by endotoxin or other substances.

NOS inhibitors and especially specific inhibitors of NOS 1, NOS 2 or NOS 3 are therefore suitable for treatment of different diseases, which are induced or aggravated by pathological concentrations of NO in cells.

A number of reviews provide information on the action and inhibitors of NO-synthases. There can be mentioned, for example: Drugs 1998, 1, 321 or Current Pharmac. Design 1997, 3, 447.

As NOS inhibitors, various compounds are known. For example, arginine derivatives, aminopyridines, cyclic amidine derivatives, phenylimidazoles, etc., are described.

It has now been found that the heterocycles that are substituted according to the invention can be used especially advantageously as pharmaceutical agents compared to known compounds.

The invention relates to the compounds of Formula I, their tautomeric and isomeric forms or salts

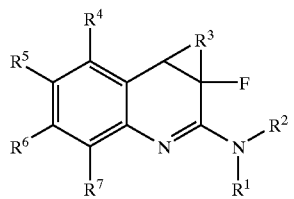

(I)

in which $R^1$ and $R^2$, independently of one another, mean:
a) Hydrogen,
b) $C_{1-6}$ alkyl,
c) $OR^8$,
d) $NR^8R^9$,
e) CN,
f) acyl,
g) $CO_2R^{10}$,
h) $CONR^8R^9$,
i) $CSNR^8R^9$, $R^3$ means:
a saturated or unsaturated $C_{1-5}$ alkylene radical, which can be substituted in 1 to 4 places with $OR^8$, $NR^{11}R^{12}$ or $C_{1-4}$ alkyl and in which 1 or 2 $CH_2$ groups can be replaced by O, $S(O)_n$, $NR^{11}$, =N— or carbonyl, and which can be bridged with a methano, ethano or propano group, $R^4$, $R^5$, $R^6$ and $R^7$, independently of one another, mean:
a) Hydrogen,
b) halogen,
c) $S(O)_n R^8$,
d) $OR^8$,
e) $COOR^8$,
f) $COR^8$,
g) $CONR^8R^{13}$,
h) $CSNR^8R^{13}$,
i) $C(NR^8)NR^9R^{13}$,
j) $NR^{14}R^{15}$,
k) $C_{1-6}$ alkyl, which optionally is substituted with halogen, $OR^8$, $SR^8$, $NR^{14}R^{15}$, phenyl, 5- to 6-membered heteroaryl with 1–4 N, S or O atoms or $C_{3-7}$ cycloalkyl,
l) $C_{3-7}$ cycloalkyl,
m) $C_{2-6}$ alkenyl, optionally substituted with phenyl or halogen,
n) $C_{2-6}$ alkinyl, optionally substituted with phenyl or halogen,
o) $C_{6-10}$ aryl, which optionally is substituted with halogen, CN, $C_{1-4}$ alkyl, $SR^8$ or $OR^8$,
p) 5- to 6-membered hetaryl with 1 to 4 N, O or S atoms, which contain a slightly condensed benzene ring and can be substituted with halogen, $NO_2$, cyano, $—OR^8$, $SR^8$, $C_{1-4}$ alkyl, $CF_3$ or $NR^8R^{13}$,
q) CN,
r) $NO_2$,
s) $CF_3$,
t) $OCF_3$, $R^4$ and $R^5$, $R^5$ and $R^6$, or $R^6$ and $R^7$ together with 2 adjacent carbon atoms form a 5- or 6-membered carbocycle, which can be substituted with $NR^{14}R^{15}$, $R^8$, $R^9$ and $R^{10}$, independently of one another, mean:
a) Hydrogen,
b) $C_{1-6}$ alkyl,
c) $C_{6-10}$ aryl, which optionally is substituted with halogen or $C_{1-4}$ alkyl, $R^{11}$ and $R^{12}$, independently of one another, mean
a) Hydrogen,
b) $C_{1-6}$ alkyl,
b) $COR^{16}$,
c) $CO_2R^{10}$,
d) $CONR^8R^9$,
e) $CSNR^8R^9$, $R^{13}$ means:
a) Hydrogen,
b) $C_{1-6}$ alkyl, optionally substituted with halogen, amino, hydroxyl or sulfhydryl groups,
c) $C_{6-10}$ aryl, $R^{14}$ and $R^{15}$, independently of one another, mean:
a) Hydrogen
b) $CO_2R^{10}$
c) $C_{1-6}$ alkyl, optionally substituted with halogen, hydroxy, $C_{1-4}$ alkoxy, nitro, amino, $C_{1-6}$ alkyl, trifluoromethyl, carboxyl, cyano, carboxamido, $C_{3-7}$ cycloalkyl, indanyl, 1,2,3,4-tetrahydronaphthyl, $C_{6-10}$ aryl, 5- or 6-membered heteroaryl with 1–4 nitrogen, oxygen or sulfur atoms, whereby the aryl and the heteroaryl radical can be substituted with halogen, hydroxy, $C_{1-4}$ alkoxy, $C_{1-4}$ alkyl, $CF_3$, $NO_2$, $NH_2$, $N(C_{1-4}$ alkyl$)_2$ or carboxyl, or $R^{14}$ and $R^{15}$ together with the nitrogen atom form a 5- to 7-membered saturated heterocycle, which can contain another oxygen, nitrogen or sulfur atom and can be substituted with $C_{1-4}$ alkyl, phenyl, benzyl or benzoyl or can contain an unsaturated 5-membered heterocycle, which can contain 1–3 N atoms and can be substituted with phenyl, $C_{1-4}$ halogen or $CH_2$—OH, $R^{16}$ means
  a) $C_{1-6}$ alkyl,
  b) $C_{6-10}$ aryl, which optionally is substituted with halogen or $C_{1-4}$ alkyl,
  and
n means 0, 1 or 2.

The compounds of the formula can be present as tautomers, stereoisomers or geometric isomers. The invention also comprises all possible isomers, such as E- and Z-isomers, S- and R-enantiomers, cis- and trans-diastereomers, racemates and mixtures thereof, including the tautomeric compounds of Formulas Ia and Ib (for $R^2$=hydrogen).

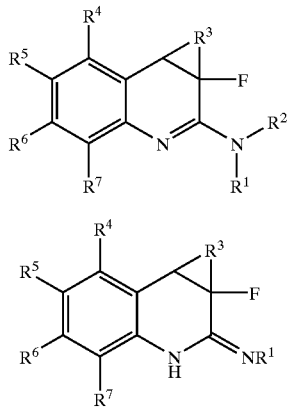

The physiologically compatible salts can be formed with inorganic and organic acids, such as, for example, oxalic acid, lactic acid, citric acid, fumaric acid, acetic acid, maleic acid, tartaric acid, phosphoric acid, hydrochloric acid, hydrobromic acid, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, or sec-hexyl.

If the alkyl radical is halogenated, the latter can be present in one or more places in halogenated form, whereby trifluoromethyl is preferred.

Alkenyl and alkinyl substituents are respectively straight-chain or branched. For example, the following radicals can be mentioned: vinyl, 2-propenyl, 1-propenyl, 1-butenyl, 2-butenyl, 3-butenyl, 2-methyl-2-propenyl, 2-pentenyl, 4-hexenyl, ethinyl, 1-propinyl, 2-propinyl, 1-butinyl, 2-butinyl.

Cycloalkyl is defined respectively as cyclopropyl, cyclobutyl, cyclopentyl, cyclohexyl or cycloheptyl.

As bicyclic compound $R^3$, for example, bicyclo[2.2.1]heptane, bicyclo[2.2.2]octane, or bicyclo[3.2.1]octane is considered.

Halogen means respectively fluorine, chlorine, bromine or iodine.

Aryl is defined respectively as naphthyl or especially phenyl, which can be substituted in one to three places. The phenyl and benzyl radicals can also be substituted by the same or a different component in one to three places.

In each case, the heteroaryl radical can contain a slightly condensed benzene ring and can be substituted by the same or a different component in one to three places and can be bonded via the heteroatom or a carbon atom. For example, the following 5- and 6-ring heteroaromatic compounds are suitable: Imidazole, indole, isoxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline.

Preferred are 5- and 6-membered heteroaromatic compounds with 1 to 2 nitrogen, oxygen and sulfur atoms and especially thienyl and furanyl, such as 2-furanyl. As substituents of the heteroaryl radicals, especially $NO_2$, CN, halogen, $C_{1-4}$ alkyl and $CF_3$ are suitable.

As saturated heterocycles $NR^{14}R^{15}$, for example, piperidine, pyrrolidine, morpholine, thiomorpholine, hexahydroazepine and piperazine can be mentioned. The heterocycle can be substituted in 1 to 3 places with $C_{1-4}$ alkyl or a phenyl, benzyl or benzoyl radical that is optionally substituted with halogen. For example, there can be mentioned: N-methyl-piperazine, 2,6-dimethylmorpholine, phenylpiperazine or 4-(4-fluorobenzoyl)-piperidine.

If $NR^{14}R^{15}$ together with the nitrogen atom form an unsaturated heterocycle, there can be mentioned, for example, imidazole, pyrrole, pyrazole, triazole, benzimidazole and indazole, which can be substituted in one to two places with phenyl, $C_{1-4}$ alkyl, halogen, especially chlorine, or $CH_2$—OH.

If $R^{14}$ or $R^{15}$ means indanyl or 1,2,3,4-tetrahydronaphthyl, this radical can be linked respectively in 1- or 2-position.

If $R^4/R^5$, $R^5/R^6$ or $R^7/R^8$ together with 2 adjacent carbon atoms form a carbocyclic compound, the latter can be substituted in any position in one or two places with $NR^{14}R^{15}$. Simple substitution is preferred. $R^4/R^5$, $R^5/R^6$ or $R^7/R^8$ preferably mean $C_{3-4}$ alkylene, whereby $R^5/R^6$ substitution is preferred.

The acyl radical is derived from straight-chain or branched aliphatic $C_1$–$C_6$ carboxylic acids, such as, for example, formic acid, acetic acid, propionic acid, butyric acid, trimethylacetic acid or caproic acid, or from known benzenesulfonic acids, which can be substituted with halogen or $C_{1-4}$ alkyl, and $C_{1-4}$ alkanesulfonic acids suitable, such as, for example, methanesulfonic acid, and p-toluenesulfonic acid. Preferably alkanoyls can be mentioned.

As preferred embodiments of $R^1$ and $R^2$, $R^1$ can be viewed in the meaning of hydrogen, and in particular $R^1$ and $R^2$ mean hydrogen.

$R^3$ preferably means alkylene with 1 to 5 carbon atoms, in which 1 or 2 $CH_2$ groups can be replaced by O or S and especially $C_{1-5}$ alkylene. For example, —$CH_2$—O—$CH_2$—, —$CH_2$—S—$CH_2$—, —$(CH_2)_3$—, —$(CH_2)_4$— and —$(CH_2)_5$— can be mentioned.

In particular, 1–2 substituents $R^4$, $R^5$, $R^6$ and $R^7$ are present, which do not mean hydrogen.

Preferred embodiments of $R^4$, $R^5$, $R^6$ and $R^7$ are:
  a) Hydrogen,
  b) halogen,
  c) $SR^8$,
  d) $OR^8$,
  e) $COOR^8$,
  f) $COR^8$, g) $CONR^8R^{13}$, h) $NR^{14}R^{15}$, i) $C_{1-6}$ alkyl, which optionally is substituted with halogen, $OR^8$, $SR^8$, $NR^{14}R^{15}$, phenyl, 5- to 6-membered heteroaryl with 1–4 N, S or O atoms or $C_{3-7}$ cycloalkyl, j) phenyl, which optionally is substituted with halogen, CN, $C_{1-4}$ alkyl, $SR^8$ or $OR^8$, k) 5- to 6-membered heteroaryl with 1 to 4 N, O or S atoms, which contain a slightly condensed benzene ring and can be substituted with halogen, $NO_2$, cyano, $C_{1-4}$ alkyl, $CF_3$ or $NR^8R^{13}$, l) CN, m) $NO_2$, n) $CF_3$, o) $OCF_3$ or p) $R^4$ and $R^5$, $R^5$ and $R^6$, or $R^6$ and $R^7$ together with 2 adjacent carbon atoms form a 5- or 6-membered carbocyclic compound, which can be substituted with $NR^{14}R^{15}$.

Especially preferred embodiments of $R^4$, $R^5$, $R^6$ and $R^7$ are:

a) Hydrogen, b) halogen, c) $SR^8$, d) $OR^8$, e) $NR^{14}R^{15}$, f) $C_{1-6}$ alkyl, which optionally is substituted with halogen, $OR^8$, $NR^{14}R^{15}$, phenyl, 5- to 6-membered heteroaryl with 1–4 N, S or O atoms or $C_{3-7}$ cycloalkyl, g) phenyl, which optionally is substituted with halogen, CN, $C_{1-4}$ alkyl, or $OR^8$, h) 5- to 6-membered heteroaryl with 1 to 4 N, O or S atoms, which contain a slightly condensed benzene ring and can be substituted with halogen, $NO_2$, cyano, $C_{1-4}$ alkyl, $CF_3$ or $NR^8R^{13}$, i) CN, j) $NO_2$, k) $CF_3$, l) $OCF_3$ or m) $R^4$ and $R^5$, $R^6$ and $R^7$, or in particular $R^5$ and $R^6$ together with 2 adjacent carbon atoms form a 5- or 6-membered carbocyclic compound, which can be substituted with $NR^{14}R^{15}$.

Preferred embodiments of $R^{14}$ and $R^{15}$ are:

a) Hydrogen, b) $C_{1-6}$ alkyl, optionally substituted with halogen, hydroxy, $C_{1-4}$ alkoxy, nitro, amino, $C_{1-6}$ alkyl, trifluoromethyl, carboxyl, cyano, carboxamido, phenyl, 5- or 6-membered heteroaryl with 1–4 nitrogen, oxygen or sulfur atoms, whereby the phenyl radical and the heteroaryl radical can be substituted with halogen, hydroxy, $C_{1-4}$ alkoxy, $C_{1-4}$ alkyl, $CF_3$, $NO_2$, $NH_2$, $N(C_{1-4}$ alkyl$)_2$ or carboxyl.

The invention also relates to the use of the compounds according to the invention for the production of a pharmaceutical agent for treating diseases that are caused by the action of nitrogen monoxide at pathological concentrations. These include neurodegenerative diseases, inflammatory diseases, auto-immune diseases, and cardiovascular diseases.

For example, there can be mentioned: cerebral ischemia, hypoxia and other neurodegenerative diseases, which are brought into contact with inflammations, such as multiple sclerosis, amyotrophic lateral sclerosis and comparable sclerotic diseases, Parkinson's Disease, Huntington's Disease, Korksakoff's Disease, epilepsy, vomiting, stress, sleep disorders, schizophrenia, depression, migraine, pain, hypoglycemia, dementia, such as, e.g., Alzheimer's Disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc.

Based on their profile of action, the compounds according to the invention are very well suited for inhibiting the neuronal NOS.

To use the compounds according to the invention as pharmaceutical agents, they are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions; elixirs, aerosols or emulsions or rectally in the form of suppositories or in the form of injection solutions that can also optionally be used subcutaneously, intramuscularly or intravenously, or topically also in the form of transdermal systems and sprays or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, vegetable oils, polyalkylene glycols, etc. Moreover, preservatives, stabilizers, wetting agents, emulsifiers or salts for changing the osmotic pressure or buffers optionally can be contained.

For parenteral administration, especially injection solutions or suspensions, especially aqueous solutions of the active compounds in polyhydroxyethoxylated castor oil, are suitable.

As vehicle systems, surface-active adjuvants such as salts of bile acids or animal or plant phospholipids, but also mixtures thereof as well as liposomes or their components can be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredients can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into 2 or more daily doses.

The NOS-inhibitory action of the compounds of Formula (I) and their physiologically compatible salts can be determined according to the methods by Bredt and Snyder in Proc. Natl. Acad. Sci. USA (1989) 86, 9030–9033. The bNOS inhibition of the compound described in Example 2 (4-amino-3a,6-difluoro-2,3,3a,9b-tetrahydro-1H-cyclopenta[c]quinoline) is $IC_{50}$=590 nM.

The production of the compounds according to the invention is carried out in that a compound of formula (II) or its salt

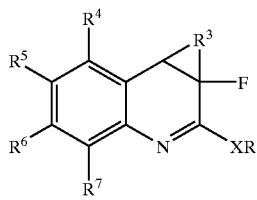

(IIa)

or

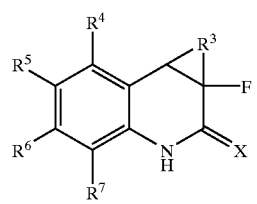

(IIb)

in which R³ to R⁷ have the above meaning, R is methyl or ethyl and X is oxygen or sulfur, is reacted with ammonia, primary or secondary amines, hydroxylamine and its derivatives or hydrazine and its derivatives, and optionally then the isomers are separated or the salts are formed.

The reaction with ammonia is possible under pressure in autoclaves with excess ammonia at low temperatures (−78° C.) or by stirring in methanol that is saturated with ammonia. Thiolactams are preferably reacted. If the reaction is carried out with amines, first the iminoethers or iminothioethers are produced from lactam or thiolactam as intermediate compounds (e.g., with methyl iodide or dimethyl sulfate), and the latter are reacted with or without isolation with the corresponding amines or their salts.

The isomer mixtures can be separated into enantiomers or E/Z-isomers according to commonly used methods, such as, for example, crystallization, chromatography or salt formation. The enantiomers can also be obtained by chromatography on chiral phases as well as by stereoselective syntheses.

The production of the salts is carried out in the usual way, by a solution of the compound of Formula (I) being mixed with the equivalent amount of acid or excess acid, which optionally is in solution, and the precipitate being separated or the solution being worked up in the usual way.

If the production of the starting compounds is not described, the latter are known and commercially available or can be produced analogously to known compounds or according to processes that are described here.

In the precursor stages, optionally sulfides are oxidized, esters are saponified, acids are esterified, hydroxy groups are etherified or acylated, amines are acylated, alkylated, diazotized, halogenated, NO₂ is introduced or reduced, reacted with isocyanates or isothiocyanates, the isomers are separated or the salts are formed.

The saponification of an ester group can be done in a basic or acidic manner by hydrolysis being performed at room temperature or at a higher temperature up to the boiling point of the reaction mixture in the presence of alkali hydroxides in ethanol or other alcohols or using acids such as, e.g., hydrochloric acid, and optionally salts of 3,4-cycloalkanodihydroquinolines are further processed.

The esterification of carboxylic acid is carried out in a way that is known in the art with diazomethane or the corresponding alcohol in acid or in the presence of an activated acid derivative. As activated acid derivatives, for example, acid chloride, acid imidazolide or acid anhydride are suitable.

In addition, a nitro group or halogen, especially bromine, can be introduced by electrophilic aromatic substitution. Mixtures that are produced in this case can be separated in the usual way, even using HPLC. If a nitrile is present, the latter can be saponified according to known processes or can be introduced into the corresponding amine, tetrazole or amidoxime.

The Friedel-Crafts acylation is used successfully in lactams of type (IIb, X=O); then the lactam can be converted selectively into the thiolactam.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water, acetic acid or concentrated sulfuric acid as a solvent is also possible at temperatures of between −10° C. and 30° C.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate or formic acid can also be used in a known way. Reducing agents such as tin(II) chloride or titanium(III) chloride can also be used, such as complex metal hydrides, optionally in the presence of heavy metal salts. For nitro groups, reduction with zinc in water-ethanol-THF/ ammonium chloride or iron in acetic acid has proven its value.

If a single or multiple alkylation of an amino group or a CH-acid carbon position is desired, alkylation can be performed with, for example, alkyl halides according to commonly used methods. Protection of the lactam group as an anion by a second equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids, such as hydrochloric acid or hydrobromic acid, or being reacted with potassium iodide.

Thiolactams of Formula (IIb, X=S) are obtained, for example, from lactams with phosphorus pentasulfide ($P_4S_{10}$) or 2,4-bis(4-methoxyphenyl)-1,3,2,4-dithiaphosphetane-2, 4-disulfide (Lawesson's reagent) in suitable solvents. Compounds of Formula (IIa) can be obtained by, for example, reaction with Meerwein reagent (trimethyloxonium tetrafluoroborate).

The invention also relates to the compounds of Formula IIb

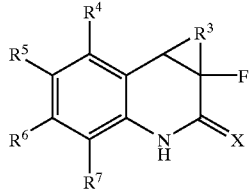

(IIb)

in which $R^3$ to $R^7$ have the above meaning, and X is oxygen or sulfur, that represent intermediate compounds during the production of pharmacologically active compounds.and are obtained and further processed according to the described processes.

The production of the compounds of Formula (IIb, X=O) is carried out, for example, in that a compound of Formula (III)

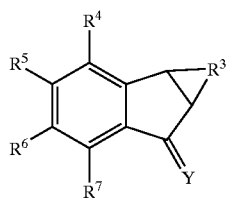

(III)

in which $R^3$ to $R^7$ have the above meaning and Y=O, after conversion into the oxime (Y=NOH), for example with a hydroxylammonium salt and sodium acetate, is subjected to a Beckman rearrangement (R. E. Gawley, Org. Reactions 1988, 35, 1), for example in polyphosphoric acid (cf. K. Hino, Y. Nagai, H. Uno, Cham, Pharm, Bull. 1998, 36, 2386) and then optionally fluorinated after a protective group is introduced.

Another synthesis method starts from a compound of Formula (IV),

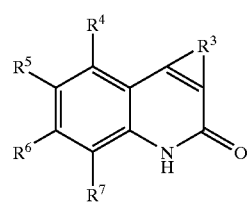

(IV)

which is reduced to lactam with an alkali or alkaline-earth metal or an amalgam thereof in alcohol (cf. B. K. Blount, W. H. Perkin, S. G. P. Plant, J. Chem. Soc. 1929, 1975, R. Brettle, S. M. Shibib, J. Chem. Soc. Perkin Trans. 1, 1981, 2912).

The invention also relates to the compounds of Formula IVa

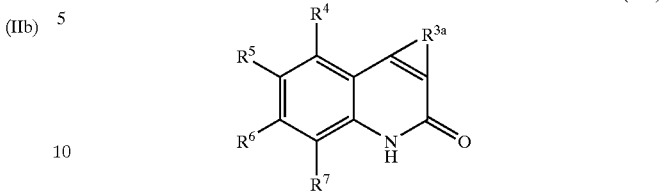

(IVa)

in which $R^{3a}$ is —$(CH_2)_3$— and $R^4$, $R^5$, $R^6$ and $R^7$ have the above meaning, whereby $R^4$–$R^7$ does not simultaneously mean hydrogen, that represent intermediate compounds during the production of pharmacologically active compounds, and are obtained and further processed according to the described process.

The subsequent fluorination to a compound of Formula II can be performed with N-fluoro-(phenylsulfonyl)imide with the alkali metal-enolate in solvents such as cyclic ethers. Before the fluorination, a protective group such as tert-butoxycarbonyl is advantageously introduced, which is cleaved off in the usual way after fluorination.

The production of indanones of type (III) is carried out in the way that is known to one skilled in the art, e.g., according to W. Baker, P. G. Jones, J. Chem. Soc. 1951, 787, S. Ohta, M. Yamashita, K. Arita, T. Kajiura, I. Kawasaki, K. Noda, M. Izumi, Chem. Pharm. Bull. 1995, 43, 1294; C. Santelli-Rouvier, M. Santelli, Synthesis 1983, 429.

The production of quinolones of type (IV) is carried out in the way that is known to one skilled in the art, e.g., according to B. K. Blount, W. H. Perkin, S. G. P. Plant, J. Chem. Soc. 1929, 1975; W. Ried, W. Käppeler, Liebigs Ann. Chem. 1965, .688, 177; L. A. White, R. C. Storr, Tetrahedron 1996, 52, 3117.

The production of the compound of Formula (III) can be carried out, for example, in that an aromatic compound (V) is reacted with an activated acid derivative, such as, for example, an acid chloride (Z=Cl) or anhydride (Z=OCOR) in the presence of a Lewis acid, such as, for example, $AlCl_3$, $SnCl_4$, $ZnCl_2$, $SbCl_5$, $FeCl_3$, $BF_3$-etherate, in an inert solvent, such as, for example, dichloromethane, dichloroethane or benzene at 0° C. up to the boiling point of the corresponding solvent (see, e.g., W. Baker, P. G. Jones, J. Chem. Soc. 1951, 787). As an alternative, the ketones of Formula (VII) that are produced according to methods that are known to one skilled in the art (e.g., according to S. Ohta, M. Yamashita, K. Arita, T. Kajiura, I. Kawasaki, K. Noda, M. Izumi, Chem. Pharm. Bull. 1995, 43, 1294) can be cyclized with Brönstedt acids, such as, for example, sulfuric acid, p-toluenesulfonic acid, methanesulfonic acid, phosphoric acid or polyphosphoric acid (cf. C. Santelli-Rouvier, M. Santelli, Synthesis .1983, 429).

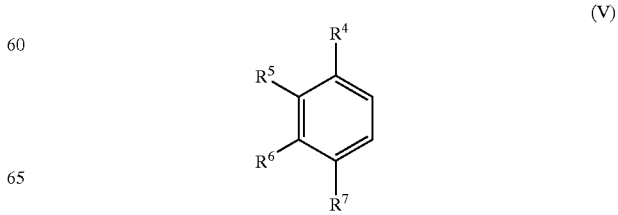

(V)

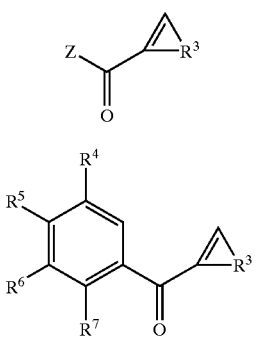

The production of the compound of Formula (IV) can be carried out, for example, in that a beta-ketoamide of Formula (VIII) or its derivative is treated with an acid, for example sulfuric acid, phosphoric acid, polyphosphoric acid or trifluoroacetic acid or methanesulfonic acid (e.g., B. K. Blount, W. H. Perkin, S. G. P. Plant, J. Chem. Soc. 1929, 1975; W. Ried, W. Käppeler, Liebigs Ann. Chem. 1965, 688, 177).

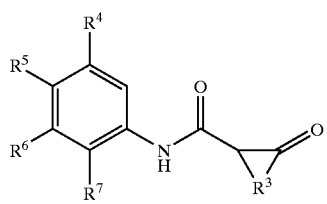

The introduction of substituents $R^4$–$R^7$ can also be carried out in the stage of compounds (III) and (IV) and takes place as described above.

For example, the production of the compounds of Formula II with $R^4$, $R^5$, $R^6$ or $R^7$ in the meaning of an alkyl radical that is substituted with $NR^{14}R^{15}$ can be carried out by reductive amination of the corresponding aldehyde or if $R^4$ and $R^5$ form a 5- or 6-membered carbocyclic compound, which is substituted with $NR^{14}R^{15}$, by reductive amination of the corresponding ketone. If the introduction of a heteroaryl radical $NR^{14}R^{15}$ is desired, the corresponding halogen derivative can be nucleophilically substituted. If a primary or secondary amino group is present, it can be advantageous to protect the latter intermediately, for example by introducing a tert-butoxycarbonyl group, which is cleaved in the usual way after the formation of amidine.

New compounds were identified by one or more of the following methods: melting point, mass spectroscopy, infrared spectroscopy, nuclear magnetic resonance spectroscopy (NMR). NMR spectra were measured with a Bruker 300 MHz device; the (deuterated) solvents are respectively indicated and abbreviated as follows: $CDCl_3$ (chloroform), $CD_3OD$ ([$D_4$]-methanol), DMSO ([$D_6$]-dimethyl sulfoxide). Alterations are indicated in delta and ppm. Here: m means multiplet, several signals; s means singlet; d means doublet; dd means double doublet, etc.; t means triplet; q means quartet; H means hydrogen protons. In addition, THF means tetrahydrofuran, DMF means N,N-dimethylformamide, MeOH means methanol, and ml means milliliter. All solvents are p.A. grade, unless otherwise indicated. All reactions are performed under cover gas, unless these are aqueous solutions. Melting points are indicated in degrees Celsius and are not corrected.

Below, the production of precursors, intermediate products and products is described by way of example.

Starting Compounds

A) 1,2,3,3a,5,9b-Hexahydrocyclopenta[c]quinolin-4-one

According to Method A 2,3,3a,8a-Tetrahydro-1H-cyclopent[a]inden-8-one (1.06 g, 6.0 mmol) (W. Baker, P. G. Jones, J. Chem. Soc. 1951, 787) is dissolved with hydroxylammonium sulfate (1.96 g, 12.0 mmol) and sodium acetate (24.0 mmol, 3.28 g) in THF-ethanol-water 1:1:1 (120 ml) and stirred for five days at room temperature. The reaction mixture is concentrated by evaporation and diluted with ethyl acetate (150 ml), washed with saturated NaCl (50 ml), dried ($Na_2SO_4$) and concentrated by evaporation in a vacuum. The residue is purified by column chromatography ($SiO_2$) with the eluant hexane-ethyl acetate. Yield: 0.88 g (78%), melting point 118–20° C.; the thus obtained oxime (0.65 g, 3.5 mmol) is added to polyphosphoric acid (10 ml) that is 120° C. The batch is stirred for 30 minutes at 120° C. After cooling, it is taken up in water (150 ml), and the aqueous solution is extracted with ethyl acetate (3×150 ml). The combined ethyl acetate extracts are dried ($Na_2SO_4$) and concentrated by evaporation in a vacuum. The residue is purified by column chromatography ($SiO_2$) with the eluant hexane-ethyl acetate.

Yield: 202 mg (31%), melting point 133–5° C.

According to Method B 1,2,3,5-Tetrahydrocyclopenta[c]quinolin-4-one (410 mg, 2.21 mmol) (W. Ried, W. Käppeler, Liebigs Ann. Chem. 1965, 688, 177) is dissolved in methanol (25 ml) and mixed with magnesium (538 mg, 22.1 mmol). After 3 hours of stirring at room temperature, the batch is filtered, the filter residue is washed with ethyl acetate, and the combined filtrates are concentrated by evaporation. Purification by column chromatography ($SiO_2$) with the eluant hexane-ethyl acetate yields 290 mg (71%) of the product.

$^1$H-NMR ($CDCl_3$) δ=1.60–1.80 (m, 3H), 2.03–2.20 (m, 2H), 2.26–2.40 (m, 1H), 2.96 (td, 1H), 3.20–3.32 (m, 1H), 6.78 (dd, 1H), 7.00 (td, 1H), 7.17 (td, 1H), 7.21 (dd, 1H), 8.32 (br. s, 1H).

MS (EI) m/e=187 ($M^+$)

B) 5-tert-Butoxycarbonyl-3a-fluoro-1,2,3,3a,5,9b-hexahydrocyclopenta[c]quinolin-4-one A solution of 374 mg (2.0 mmol) of 1,2,3,3a,5,9b-hexahydrocyclopenta[c]quinolin-4-one in 50 ml of THF is mixed at room temperature with 655 mg (3.0 mmol) of pyrocarbonic acid-di-tert-butylester and 367 mg (3.0 mmol) of 4-(dimethylamino)-pyridine. After 64 hours at room temperature, the reaction mixture is concentrated by evaporation, and the residue is purified by column chromatography on silica gel with hexane-ethyl acetate. In this case, 350 mg of 5-tert-butoxycarbonyl-1,2,3,3a,5,9b-hexahydrocyclopenta[c]quinolin-4-one is isolated:

$^1$H-NMR ($CDCl_3$): 1.43–1.83 (m, 3H), 1.63 (s, 9H), 1.95–2.12 (m, 2H), 2.44 (m, 1H), 2.98 (td, 1H), 3.20 (q, 1H), 6.82 (dd, 1H), 7.06 (td, 1H), 7.20 (td, 1H), 7.24 (dd, 1H).

1.5 ml (2.4 mmol) of n-butyllithium (1.6 M in hexane) is added in drops at −70° C. to a solution that consists of 0.25 ml (2.4 mmol) of diethylamine in 20 ml of THF. After ¾ hour at −70° C., a solution of 350 mg (1.2 mmol) of 5-tert-butoxycarbonyl-1,2,3,3a,5,9b-hexahydrocyclopenta[c]quinolin-4-one in 10 ml of THF is added to it. The batch is stirred for 1 hour at −70° C., then mixed with 1.13 g (3.6 mmol) of N-fluoro-(phenylsulfonyl)imide and heated within 3 hours to room temperature. After 2 days of stirring at room temperature, the reaction mixture is concentrated by evaporation and purified by column chromatography on silica gel with hexane-ethyl acetate: 360 mg of product.

$^1$H-NMR (CDCl$_3$) 1.62 (s, 9H), 1.86–2.29 (m, 5H), 2.41 (m, 1H), 3.62 (dm, 1H), 6.84 (d, 1H), 7.12 (t, 1H), 7.21 (d, 1H), 7.27 (t, 1H).

C) 3a-Fluoro-1,2,3,3a,5,9b-hexahydrocyclopenta[c]quinolin-4-one

A solution of 350 mg (1.1 mmol) of 5-tert-butoxycarbonyl-3a-fluoro-1,2,3,3a,5,9b-hexahydrocyclopenta[c]quinolin-4-one in 5 mL of dichloromethane is mixed with 5 ml of trifluoroacetic acid at room temperature. After 1 hour, the batch is diluted with water (100 ml) and ethyl acetate (100 ml). The organic phase is separated, washed with water (50 ml), saturated NaHCO$_3$, (2×50 ml) and saturated NaCl (50 ml), dried (Na$_2$SO$_4$) and concentrated by evaporation in a vacuum. Column chromatography of the residue on silica gel with hexane-ethyl acetate yields 160 mg of product.

$^1$H-NMR (CDCl$_3$) 1.72 (m, 1H), 1.90–2.55 (m, 5H), 3.64 (dt, 1H), 6.89 (d, 1H), 7.08 (t, 1H), 7.20 (d, 1H), 7.24 (t, 1H), 8.93 (br.s, NH).

MS (EI) m/e=205 (M$^+$)

D) 3a-Fluoro-1,2,3,3a,5,9b-hexahydrocyclopenta[c]quinoline-4-thione

A solution of 150 mg (0.73 mmol) of 3a-fluoro-1,2,3,3a,5,9b-hexahydrocyclopenta[c]quinolin-4-one in 50 ml of THF is mixed with 607 mg (1.5 mmol) of Lawesson's reagent. After 1 hour of stirring at room temperature, the batch is refluxed for 2 hours. Then, the reaction mixture is concentrated by evaporation and the residue is purified by column chromatography on silica gel (eluant: hexane-ethyl acetate): 150 mg of product.

$^1$H-NMR (CDCl$_3$): 1.69 (m, 1H), 1.88–2.62 (m, 5H), 3.56 (dd, 1H), 6.89 (dd, 1H), 7.16 (td, 1H), 7.22 (d, 1H), 7.27 (t, 1H), 9.79 (br.s, NH).

MS (EI) m/e=221 (M$^+$)

EXAMPLE 1

4-Amino-3a-fluoro-2,3,3a,9b-tetrahydro-1H-cyclopenta[c]quinoline 142 mg (0.64 mmol) of 3a-fluoro-1,2,3,3a,5,9b-hexahydrocyclopenta[c]quinoline-4-thione is dissolved in 50 ml of 7 M methanolic ammonia solution. After 1 hour of stirring at room temperature, the batch is concentrated by evaporation in a vacuum, and the residue is purified by column chromatography on silica gel with dichloromethane-ethanol as an eluant: 108 mg of product, melting point 174–6° C.

$^1$H-NMR (CDCl$_3$): 1.68 (m, 1H), 1.77–2.01 (m, 2H), 2.09–2.51 (m, 3H), 3.53 (dd, 1H), 4.34 (br., 2H), 7.00 (t, 1H), 7.04 (d, 1H), 7.16 (t, 1H), 7.19 (d, 1H).

MS (EI) m/e=204 (M$^+$)

EXAMPLE 2

4-Amino-3a,6-difluoro-2,3,3a,9b-tetrahydro-1H-cyclopenta[a]quinoline

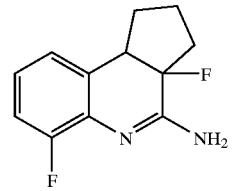

5-tert-Butoxycarbonyl-3a,6-difluoro-1,2,3,3a,5,9b-hexahydrocyclopenta[c]quinolin-4-one A solution of 180 mg (0.9 mmol) of 6-fluoro-1,2,3,3a,5,9b-hexahydrocyclopenta[c]quinolin-4-one (WO99/41240) in 10 ml of THF is mixed at room temperature with 284 mg (1.3 mmol) of pyrocarbonic acid-di-tert-butylester and 158 mg (3.0 mmol) of 4-(dimethylamino)pyridine. After 48 hours at room temperature, the reaction mixture is concentrated by evaporation, and the residue is purified by column chromatography on silica gel with hexane-ethyl acetate. In this case, 240 mg (0.8 mmol) of 5-tert-butoxycarbonyl-6-fluoro-1,2,3,3a,5,9b-hexahydrocyclopenta[c]quinolin-4-one is isolated, which is dissolved in 20 ml of THF. At −70° C., 3.2 mL (1.6 mmol) of a 0.5 M potassium hexamethyldisilazide-toluene solution is added in drops to it. The batch is stirred for 1 hour at −70° C., then mixed with 742 mg (2.4 mmol) of N-fluoro(phenylsulfonyl)imide and stirred for 4 hours at −70° C. and for 20 hours at room temperature. The reaction mixture is diluted with ethyl acetate, washed with water, dried (Na$_2$SO$_4$) and concentrated by evaporation in a vacuum. Column chromatography on silica gel with hexane-ethyl acetate yields 200 mg of product.

$^1$H-NMR (CDCl$_3$): 1.55–1.70 (m, 1H), 1.62 (s, 9H), 1.90–2.50 (m, 5H), 3.66 (dm, 1H), 7.00–7.18 (m, 3H).

3a,6-Difluoro-1,2,3,3a,5,9b-hexahydrocyclopenta[c]quinolin-4-one

A solution of 200 mg (0.6 mmol) of 5-tert-butoxycarbonyl-3a,6-difluoro-1,2,3,3a,5,9b-hexahydrocyclopenta[c]quinolin-4-one in 2 ml of dichloromethane is mixed with 2 ml of trifluoroacetic acid at room temperature. After 30 minutes, the batch is diluted with water and ethyl acetate. The organic phase is separated, washed with water, saturated NaHCO$_3$ and saturated NaCl, dried (Na$_2$SO$_4$) and concentrated by evaporation in a vacuum. Column chromatography of the residue on silica gel with hexane-ethyl acetate yields 60 mg of product.

$^1$H-NMR (CDCl$_3$): 1.72 (m, 1H), 1.91–2.57 (m, 5H), 3.68 (dt, 1H), 6.93–7.08 (m, 3H), 7.63 (br.s, NH).

3a,6-Difluoro-1,2,3,3a,5,9b-hexahydrocyclopenta[c]quinoline-4-thione

A solution of 60 mg (0.27 mmol) of 3a,6-difluoro-1,2,3,3a,5,9b-hexahydrocyclopenta[c]quinolin-4-one in 15 ml of THF is mixed with 288 mg (0.71 mmol) of Lawesson's reagent and refluxed for 1.5 hours. Then, the reaction mixture is concentrated by evaporation, and the residue is purified by column chromatography on silica gel (eluant: hexane-ethyl acetate): 50 mg of product.

$^1$H-NMR (CDCl$_3$): 1.71 (m, 1H), 1.918–2.62 (m, 5H), 3.56 (dm, 1H), 6.98–7.15 (m, 3H), 9.39 (br.s, NH).

4-Amino-3a,6-difluoro-2,3,3a,9b-tetrahydro-1H-cyclopenta[c]quinoline 50 mg (0.21 mmol) of 3a-fluoro-1,2,3,3a,5,9b-hexahydrocyclopenta[c]quinoline-4-thione is dissolved in 15 ml of 7 M methanolic ammonia solution. After 1 hour of stirring at room temperature, the batch is concentrated by evaporation in a vacuum, and the residue is purified by column chromatography on silica gel with dichloromethane-ethanol as an eluant: 25 mg of product.

$^1$H-NMR (CDCl$_3$): 1.69 (m, 1H), 1.92 (m, 2H), 2.20 (m, 1H), 2.33 (m, 1H), 2.46 (m, 1H), 3.52 (dd, 1H), 5.86 (br., 2H), 6.88–7.02 (m, 3H).

MS (EI) m/e=222 (M$^+$)

EXAMPLE 3

4-Amino-8-bromo-3a-fluoro-2,3,3a,9b-tetrahydro-1H-cyclopenta[c]quinoline

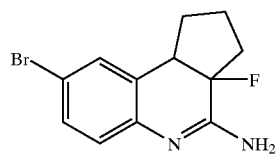

5-tert-Butyloxycarbonyl-8-bromo-3a-fluoro-1,2,3,3a,5,9b-hexahydrocyclopenta[c]quinolin-4-one A solution of 1.53 g (5.75 mmol) of 8-bromo-1,2,3,3a,5,9b-hexahydrocyclopenta[c]quinolin-4-one (WO 99/41240) in 120 ml of THF is mixed at room temperature with 1.88 g (8.63 mmol) of pyrocarbonic acid-di-tert-butylester and 1.05 g (8.63 mmol) of 4-(dimethylamino)pyridine. After 5 days at room temperature, the reaction mixture is concentrated by evaporation, and the residue is purified by column chromatography on silica gel with hexane-ethyl acetate. In this case, 1.83 g of 5-tert-butoxy-carbonyl-8-bromo-1,2,3,3a,5,9b-hexahydrocyclopenta[c]quinolin-4-one is isolated: MS (EI) m/e=365/367 (M$^+$)

9.4 ml (15.0 mmol) of n-butyllithium (1.6 M in hexane) is added in drops at −70° C. to a solution that consists of 1.56 ml (15.0 mmol) of diethylamine in 100 ml of THF. After 1 hour at −70° C., a solution of 1.83 g (5.0 mmol) of 5-tert-butoxycarbonyl-8-bromo-1,2,3,3a,5,9b-hexahydrocyclopenta[c]quinolin-4-one in 20 ml of THF is added to it. The batch is stirred for 1 hour at −70° C., then mixed with 6.30 g (20.0 mmol) of N-fluoro(phenylsulfonyl)imide and heated within 1 hour to room temperature. After 15 hours of stirring at room temperature, the reaction mixture is concentrated by evaporation and purified by column chromatography on silica gel with hexane-ethyl acetate: 1.38 g of product.

MS (EI) m/e=383/385 (M$^+$)

8-Bromo-3a-fluoro-1,2,3,3a,5,9b-hexahydrocyclopenta[c]quinolin-4-one

A solution of 1.38 g (3.6 mmol) of 5-tert-butoxycarbonyl-8-bromo-3a-fluoro-1,2,3,3a,5,9b-hexahydrocyclopenta[c]quinolin-4-one in 7 ml of dichloromethane is mixed with 7 ml of trifluoroacetic acid at room temperature. After 2 hours, the batch is diluted with water and ethyl acetate. The organic phase is separated, washed with water, saturated NaHCO$_3$ and saturated NaCl, dried (Na$_2$SO$_4$) and concentrated by evaporation in a vacuum. Column chromatography of the residue on silica gel with hexane-ethyl acetate yields 0.74 g of product.

$^1$H-NMR (CDCl$_3$): 1.73 (m, 1H), 1.90–2.54 (m, 5H), 3.62 (dt, 1H), 6.81 (d, 1H), 7.32 (d, 1H), 7.38 (s, 1H), 9.33 (br.s, NH).

MS (EI) m/e=283/285 (M$^+$)

8-Bromo-3a-fluoro-1,2,3,3a,5,9b-hexahydrocyclopenta[c]quinoline-4-thione

A solution of 0.74 g (2.6 mmol) of 8-bromo-3a-fluoro-1,2,3,3a,5,9b-hexahydrocyclopenta[c]quinolin-4-one in 100 ml of THF is refluxed with 2.16 g (5.34 mmol) of Lawesson's reagent for 1.5 hours. Then, the reaction mixture is concentrated by evaporation, and the residue is purified by column chromatography on silica gel with hexane-ethyl acetate: 0.59 g of product.

$^1$H-NMR (CDCl$_3$): 1.70 (m, 1H), 1.91–2.61 (m, 5H), 3.54 (dm, 1H), 6.81 (d, 1H), 7.37 (d, 1H), 7.43 (s, 1H), 9.91 (br.s, NH).

MS (EI) m/e=299/301 (M$^+$)

4-Amino-8-bromo-3a-fluoro-2,3,3a,9b-tetrahydro-1H-cyclopenta[c]quinoline 75 mg (0.25 mmol) of 8-bromo-3a-fluoro-1,2,3,3a,5,9b-hexahydrocyclopenta[c]quinoline-4-thione is dissolved in 20 ml of 7 M methanolic ammonia solution. After 1.5 hours of stirring at room temperature, the batch is concentrated by evaporation in a vacuum and the residue is purified by column chromatography on silica gel with ethyl acetate: 60 mg of product, melting point 220° C.

$^1$H-NMR (CDCl$_3$): 1.61–2.00 (m, 3H), 2.10–2.52 (m, 3H), 3.50 (dd, 1H), 5.40 (br., 2H), 6.92 (d, 1H), 7.27 (m, 2H).

MS (EI) m/e=282/284 (M$^+$).

EXAMPLE 4

4-Amino-8-chloro-3a-fluoro-2,3,3a,9b-tetrahydro-1H-cyclopenta[c]quinoline

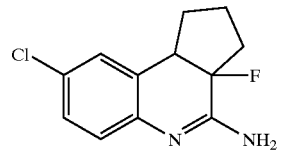

5-tert-Butyloxycarbonyl-8-chloro-3a-fluoro-1,2,3,3a,5,9b-hexahydrocyclopenta[c]quinolin-4-one A solution of 1.70 g (7.66 mmol) of 8-chloro-1,2,3,3a,5,9b-hexahydrocyclopenta[c]quinolin-4-one (WO 99/41240) in 120 ml of THF is mixed at room temperature with 2.50 g (11.5 mmol) of pyrocarbonic acid-di-tert-butyl ester and 1.40 g (11.5 mmol) of 4-(dimethylamino)pyridine. After 22 hours at room temperature, the reaction mixture is concentrated by evaporation, and the residue is purified by column chromatography on silica gel with hexane-ethyl acetate. In this case, 2.35 g of 5-tert-butoxycarbonyl-8-chloro-1,2,3,3a,5,9b-hexahydrocyclopenta[c]quinolin-4-one is isolated:

¹H-NMR (CDCl₃): 1.59–1.86 (m, 3H), 1.63 (s, 9H), 2.07 (m, 2H), 2.45 (m, 1H), 2.99 (td, 1H), 3.20 (q, 1H), 6.78 (d, 1H), 7.19 (dd, 1H), 7.24 (dd, 1H).

13.4 ml (21.5 mmol) of n-butyllithium (1.6 M in hexane) is added in drops to a solution that consists of 2.24 ml (21.5 mmol) of diethylamine in 100 ml of THF at −70° C. After 1 hour at −70° C., a solution of 2.30 g (7.2 mmol) of 5-tert-butoxycarbonyl-8-chloro-1,2,3,3a,5,9b-hexahydrocyclopenta[c]quinolin-4-one in so ml of THF is added to it. The batch is stirred for 1 hour at −70° C., then mixed with 9.02 g (28.6 mmol) of N-fluoro(phenylsulfonyl) imide and heated within 1 hour to room temperature. After 15 hours of stirring at room temperature, the reaction mixture is concentrated by evaporation and purified by column chromatography on silica gel with hexane-ethyl acetate: 2.20 g of product.

¹H-NMR (CDCl₃): 1.58–1.74 (m, 1H), 1.65 (s, 9H), 1.90–2.50 (m, 5H), 3.60 (dm, 1H), 6.82 (d, 1H), 7.20 (dd, 1H), 7.26 (d, 1H).

8-Chloro-3a-fluoro-1,2,3,3a,5,9b-hexahydrocyclopenta[c]quinolin-4-one

A solution of 2.20 g (6.5 mmol) of 5-tert-butoxycarbonyl-8-chloro-3a-fluoro-1,2,3,3a,5,9b-hexahydrocyclopenta[c]quinolin-4-one in 10 ml of dichloromethane is mixed with 10 ml of trifluoroacetic acid at room temperature. After 2 hours, the batch is diluted with water and ethyl acetate. The organic phase is separated, washed with water, saturated NaHCO₃ and saturated NaCl, dried (Na₂SO₄) and concentrated by evaporation in a vacuum. Column chromatography of the residue on silica gel with hexane-ethyl acetate yields 0.83 g of product.

¹H-NMR (CDCl₃, [D]₆-DMSO): 1.48 (m, 1H), 1.62–2.26 (m, 5H), 3.32 (dt, 1H), 6.66 (d, 1H), 6.87 (d, 1H), 6.94 (s, 1H), 10.10 (br.s, NH).

MS (El) m/e=239 (M⁺)

8-Chloro-3a-fluoro-1,2,3,3a,5,9b-hexahydrocyclopenta[c]quinoline-4-thione

A solution of 0.83 g (3.5 mmol) of 8-chloro-3a-fluoro-1,2,3,3a,5,9b-hexahydrocyclopenta[c]quinolin-4-one in 100 ml of THF is refluxed with 2.86 g (7.1 mmol) of Lawesson's reagent for 1.5 hours. Then, the reaction mixture is concentrated by evaporation, and the residue is purified by column chromatography on silica gel with hexane-ethyl acetate: 0.86 g of product.

MS (El) m/e=255 (M⁺)

4-Amino-8-chloro-3a-fluoro-2,3,3a,9b-tetrahydro-1H-cyclopenta[c]quinoline 90 mg (0.35 mmol) of 8-chloro-3a-fluoro-1,2,3,3a,5,9b-hexahydrocyclopenta[c]quinoline-4-thione is dissolved in 20 ml of 7 M methanolic ammonia solution. After 2 hours of stirring at room temperature, the batch is concentrated by evaporation in a vacuum, and the residue is purified by column chromatography on silica gel with ethyl acetate: 73 mg of product, melting point 223° C.

¹H-NMR (CDCl₃, [D₆]-DMSO): 1.39 (m, 1H), 1.60 (m, 2H), 1.83–2.02 (m, 2H), 2.15 (m, 1H), 3.17 (dd, 1H), 6.65 (d, 1H), 6.77 (dd, 1H), 6.83 (br.s, 1H).

MS (El) m/e=238 (M⁺)

EXAMPLE 5

4-Amino-7-methylaminomethyl-3a-fluoro-2,3,3a,5,9b-tetrahydro-1H-cyclopenta[c]quinoline dihydrochloride

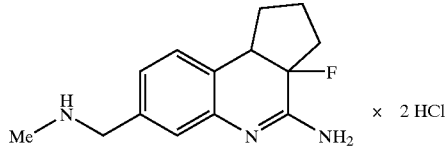

5-tert-Butyloxycarbonyl-3a-fluoro-7-(2-furanyl)-1,2,3,3a,5,9b-hexahydrocyclo-penta[c]quinolin-4-one A solution of 5.07 g (20.0 mmol) of 7-(2-furanyl)-1,2,3,3a,5,9b-hexahydro-cyclopenta[c]quinolin-4-one (WO 99/41240) in 350 ml of THF is mixed at room temperature with 6.55 g (30.0 mmol) of pyrocarbonic acid-di-tert-butyl ester and 3.67 g (30.0 mmol) of 4-(dimethylamino)pyridine. After 7 hours at room temperature, the reaction mixture is concentrated by evaporation, and the residue is purified by column chromatography on silica gel with hexane-ethyl acetate. In this case, 2.53 g of 5-tert-butoxycarbonyl-7-(2-furanyl)-1,2,3,3a,5,9b-hexahydrocyclopenta[c]quinolin-4-one is isolated:

¹H-NMR (CDCl₃): 1.65–1.80 (m, 3H), 1.65 (s, 9H), 2.08 (m, 2H), 2.43 (m, 1H), 3.00 (td, 1H), 3.22 (q, 1H), 6.48 (dd, 1H), 6.60 (d, 1H), 7.14 (d, 1H), 7.23 (d, 1H), 7.36 (dd, 1H), 7.46 (d, 1H).

10.3 ml (16.5 mmol) of n-butyllithium (1.6 M in hexane) is added in drops to a solution of 1.72 ml (16.5 mmol) of diethylamine in 100 ml of THF at −70° C. After 1 hour at −70° C., a solution of 1.94 g (5.5 mmol) of 5-tert-butoxycarbonyl-7-(2-furanyl)-1,2,3,3a,5,9b-hexahydrocyclopenta[c]quinolin-4-one in 30 ml of THF is added to it. The batch is stirred for 1 hour at −70° C., then mixed with 6.94 g (22.0 mmol) of N-fluoro(phenylsulfonyl) imide and heated to room temperature within 1 hour. After 15 hours of stirring at room temperature, the reaction mixture is concentrated by evaporation and purified by column chromatography on silica gel with hexane-ethyl acetate: 1.44 g of product.

¹H-NMR (CDCl₃): 1.65 (m, 1H), 1.68 (s, 9H), 1.87–2.52 (m, 5H), 3.65 (dm, 1H), 6.47 (dd, 1H), 6.63 (d, 1H), 7.17 (d, 1H), 7.28 (d, 1H), 7.43 (dd, 1H), 7.47 (d, 1H).

3a-Fluoro-7-(2-furanyl)-1,2,3,3a,5,9b-hexahydrocyclopenta[c]quinolin-4-one

A solution of 1.44 g (3.9 mmol) of 5-tert-butoxycarbonyl-3a-fluoro-7-(2-furanyl)-1,2,3,3a,5,9b-hexahydrocyclopenta[c]-quinolin-4-one in 20 ml of dichloromethane is mixed with 8 ml of trifluoroacetic acid at room temperature. After 2 hours, the batch is diluted with water and ethyl acetate. The organic phase is separated, washed with water, saturated NaHCO₃ and saturated NaCl, dried (Na₂SO₄) and concentrated by evaporation in a vacuum. Column chromatography of the residue on silica gel with hexane-ethyl acetate yields 0.53 g of product.

Melting point: 203–6° C.

¹H-NMR (CDCl₃) 1.73 (m, 1H), 1.91–2.55 (m, 5H), 3.65 (dm, 1H), 6.49 (dd, 1H), 6.67 (d, 1H), 7.10 (d, 1H), 7.26 (d, 1H), 7.38 (dd, 1H), 7.48 (d, 1H), 8.23 (br.s, 1H)

3a-Fluoro-1,2,3,3a,5,9b-hexahydrocyclopenta[c] quinolin-4-one-7-carboxylic acid A suspension of 0.5 g (1.8 mmol) of 3a-fluoro-7-(2-furanyl)-1,2,3,3a,5,9b-hexahydrocyclopenta[c]quinolin-4-one in 63 ml of acetonitrile-carbon tetrachloride-water (2:1:2) is mixed with 5.9 g (27.6 mmol) of sodium periodate and 0.05 g (0.4 mmol) of ruthenium(IV) oxide, and it is stirred for 4 hours at room temperature. The batch is diluted with water and extracted with ethyl acetate. The combined extracts are dried ($Na_2SO_4$) and concentrated by evaporation in a vacuum. The residue is taken up in 0.5 M potassium hydroxide solution. This solution is washed with methyl-tert-butyl ether, acidified with concentrated hydrochloric acid and extracted with ethyl acetate. The combined extracts are dried ($Na_2SO_4$) and concentrated by evaporation in a vacuum: 0.31 g of product.

$^1$H-NMR ($[D_6]$-DMSO): 1.60 (m, 1H), 1.84 (m, 1H), 1.96–2.16 (m, 3H), 2.32 (m, 1H), 3.56 (dt, 1H), 7.43 (d, 1H), 7.53 (s, 1H), 7.58 (dd, 1H), 10.71 (br.s, 1H).

7-[{N-tert-Butyloxycarbonyl)methylamino}methyl]-3a-fluoro-1,2,3,3a,5,9b-hexahydrocyclopenta[c]quinolin-4-one A solution of 0.31 g (1.24 mmol) of 3a-fluoro-1,2,3,3a,5,9b-hexahydrocyclopenta[c]quinolin-4-one-7-carboxylic acid in 35 ml of THF is treated with 0.20 ml (1.44 mmol) of triethylamine and 0.14 ml (1.44 mmol) of ethyl chloroformate. After 10 minutes at room temperature, 0.14 g (3.72 mmol) of sodium borohydride and, within 15 minutes, 19 ml of methanol, are added to it. After 15 hours, the batch is diluted with ethyl acetate, washed with 20% citric acid, dried ($Na_2SO_4$) and concentrated by evaporation in a vacuum. Column chromatography with hexane-ethyl acetate yields 3a-fluoro-7-hydroxymethyl-1,2,3,3a,5,9b-hexahydrocyclo-penta[c]quinolin-4-one, which dissolves in 50 ml of THF and is mixed at 0° C. with 4 portions each of 0.34 ml (2.5 mmol) of triethylamine and 0.19 ml (2.5 mmol) of methanesulfonyl chloride. After the reaction has been completed, the batch is poured onto ice water and extracted with ethyl acetate. The combined extracts are dried ($Na_2SO_4$) and concentrated by evaporation in a vacuum. The residue is taken up in 50 ml of 2 M methanolic methylamine solution and refluxed for 4 hours. The volatile components are removed in a vacuum, and the residue is dissolved in 50 ml of dichloromethane. 0.81 g (3.72 mmol) of pyrocarbonic acid-di-tert-butylester is added to it, and after 3 hours, another 0.40 g (1.86 mmol) is added to it. After 2 hours, the batch is diluted with dichloromethane, washed with water, dried ($Na_2SO_4$) and concentrated by evaporation in a vacuum. Column chromatography with hexane-ethyl acetate yields 49 mg of product.

$^1$H-NMR (CDCl$_3$) 1.48 (s, 9H), 1.71 (m, 1H), 1.87–2.53 (m, 5H), 2.83 (s, 3H), 3.62 (dm, 1H), 4.36 (s, 2H), 6.68 (s, 1H), 6.93 (d, 1H), 7.20 (d, 1H), 8.23/8.51 (br.s, 1H)

7-[{(N-tert-Butyloxycarbonyl) methylamino}methyl]-3a-fluoro-1,2,3,3a,5,9b-hexahydrocyclopenta[c]quinoline-4-thione A solution of 70 mg (0.2 mmol) of 7-[{(N-tert-butyloxycarbonyl)methylamino}-menthyl]-3a-fluoro-1,2,3,3a,5,9b-hexahydrocyclopenta[c]quinolin-4-one in 10 ml of THF is refluxed with 160 mg (0.4 mmol) of Lawesson's reagent for 1.5 hours. Then, the reaction mixture is concentrated by evaporation, and the residue is purified by column chromatography on silica gel with hexane-ethyl acetate: 72 mg of product.

$^1$H-NMR (CDCl$_3$): 1.49 (s, 9H), 1.68 (m, 1H), 1.89–2.61 (m, 5H), 2.84 (s, 3H), 3.53 (dm, 1H), 4.39 (s, 2H), 6.70 (s, 1H), 7.02 (d, 1H), 7.24 (d, 1H), 9.47 (br.s, 1H).

4-Amino-7-methylaminomethyl-3a-fluoro-2,3,3a,5,9b-tetrahydro-1H-cyclopenta[c]quinoline dihydrochloride 67 mg (0.18 mmol) of 7-[{(N-tert-butyloxycarbonyl) methylamino}methyl]-3a-fluoro-1,2,3,3a,5,9b-hexahydrocyclopenta[c]quinoline-4-thione is stirred in 10 ml of 7 M ammoniacal methanol for 2 hours at room temperature. After the volatile components are distilled off in a vacuum, the residue is purified by column chromatography on silica gel with dichloromethane-methanol: 52 mg (0.15 mmol) of 4-amino-7-[{(N-tert-butyloxycarbonyl) methylamino}methyl]-3a-fluoro-2,3,3a,5,9b-tetrahydro-1H-cyclopenta[c]quinoline. The latter is stirred in 2 ml of 4 M hydrochloric acidic dioxane for 1.5 hours at room temperature. The volatile components are removed in a vacuum.

MS (El) m/e=247 ([M-2 HCl]$^+$)

EXAMPLE 6

4-Amino-7-[2-(methylamino)ethyl]-3a-fluoro-2,3,3a,5,9b-tetrahydro-1H-cyclopenta[c]quinoline dihydrochloride

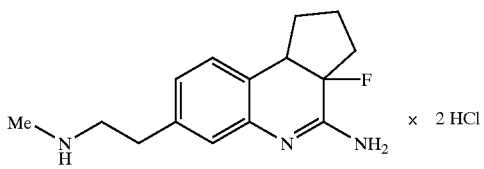

7-Vinyl-1,2,3,5-tetrahydrocyclopenta[c]quinolin-4-one

A solution of 2.0 g (7.6 mmol) of 7-bromo-1,2,3,5-tetrahydrocyclopenta[c]-quinolin-4-one, 2.6 ml (9.9 mmol) of vinyltributyltin and 0.44 g (0.38 mmol) of tetrakis (triphenylphosphine)palladium is degassed and aerated with nitrogen. After 6 hours of heating to 110° C., the batch is concentrated by evaporation and the residue is taken up on silica gel. Column chromatography on silica gel with hexane-ethyl acetate yields 1.41 g of product.

$^1$H-NMR (CDCl$_3$): 2.26 (pent., 2H), 3.05 (t, 2H), 3.16 (t, 2H), 5.41 (d, 1H), 5.91 (d, 1H), 6.82 (dd, 1H), 7.33 (d, 1H), 7.38 (s, 1H), 7.49 (d, 1H), 11.22 (br.s, 1H).

7-Oxiranyl-1,2,3,5-tetrahydrocyclopenta[c]quinolin-4-one

A solution of 1.41 g (6.7 mmol) of 7-vinyl-1,2,3,5-tetrahydrocyclopenta[c]-quinolin-4-one in 200 ml of chloroform is mixed at room temperature with mCPBA. After 15 hours at room temperature, the batch is washed with saturated $Na_2SO_3$ (2×100 ml), dried ($Na_2SO_4$) and concentrated by evaporation in a vacuum. Column chromatography on silica gel with hexane-ethyl acetate yields 0.59 g of product.

$^1$H-NMR (CDCl$_3$): 2.25 (pent., 2H), 2.85 (dd, 1H), 3.03 (t, 2H), 3.13 (t, 2H), 3.20 (dd, 1H), 3.98 (dd, 1H), 7.11 (dd, 1H), 7.35 (d, 1H), 7.49 (d, 1H), 11.44 (br.s, 1H).

7-(2-Hydroxyethyl)-1,2,3,3a,5,9b-hexahydrocyclopenta[c]quinolin-4-one

A solution of 0.59 g (2.6 mmol) of 7-oxiranyl-1,2,3,5-tetrahydrocyclopenta[c]-quinolin-4-one in 100 ml of methanol is mixed with 1.26 g (52.0 mmol) of magnesium and 0.06 ml of acetic acid. The batch is stirred for 4 hours at room temperature and mixed with another 0.63 g (26.0 mmol) of magnesium. After 15 hours at room temperature, the reaction mixture is acidified with 200 ml of 10% hydrochloric acid and extracted with ethyl acetate (3×200 ml). The combined extracts are dried ($Na_2SO_4$) and concentrated by evaporation in a vacuum. Column chromatography on silica gel with hexane-ethyl acetate yields 0.39 g of product.

$^1$H-NMR (CDCl$_3$) 1.57–1.78 (m, 3H), 2.01–2.18 (m, 2H), 2.29 (m, 1H), 2.82 (t, 2H), 2.93 (td, 1H), 3.23 (q, 1H), 3.86 (t, 2H), 6.62 (d, 1H), 6.88 (dd, 1H), 7.15 (d, 1H), 8.31 (br.s, 1H).

7-[2-(tert-Butyldimethylsilyloxy)ethyl]-1,2,3,3a,5,9b-hexahydrocyclopenta[c]quinolin-4-one At 0° C., 0.62 g (5.4 mmol) of tert-butyldimethylsilyl chloride and 0.72 g (10.7 mol) of imidazole are added to a solution of 0.62 g (2.7 mmol) of 7-(2-hydroxyethyl)-1,2,3,3a,5,9b-hexahydrocyclopenta[c]quinolin-4-one in 10 ml of DMF. After 4 hours at room temperature, the batch is diluted with ether, washed with water, 10% citric acid and saturated NaHCO$_3$, dried (Na$_2$SO$_4$) and concentrated by evaporation in a vacuum. Column chromatography with hexane-ethyl acetate on silica gel yields 0.79 g of product.

$^1$H-NMR (CDCl$_3$): 0.02 (s, 6H), 0.90 (s, 9H), 1.71 (m, 3H), 2.12 (m, 2H), 2.32 (m, 1H), 2.78 (t, 2H), 2.96 (td, 1H), 3.26 (q, 1H), 3.80 (t, 2H), 6.60 (d, 1H), 6.86 (dd, 1H), 7.14 (d, 1H), 7.93 (br.s, 1H).

5-tert-Butyloxycarbonyl-7-[2-(tert-butyldimethylsilyloxy)ethyl]-3a-fluoro-1,2,3,3a,5,9b-hexahydrocyclopenta[c]quinolin-4-one A solution of 0.79 g (2.3 mmol) of 7-[2-(tert-butyldimethylsilyloxy)ethyl]-1,2,3,3a,5,9b-hexahydrocyclopenta[c]quinolin-4-one in 60 ml of THF is stirred with 0.75 g (3.4 mmol) of pyrocarbonic acid-di-tert-butyl ester and 0.42 g (3.4 mmol) of 4-(dimethylamino)pyridine for 18 hours at room temperature. Another 0.37 g (1.7 mmol) of pyrocarbonic acid-di-tert-butyl ester and 0.21 g (1.7 mmol) of 4-(dimethylamino)pyridine are added, and after 4 hours, the solvent is removed in a vacuum, and the residue is purified by column chromatography on silica gel with hexane-ethyl acetate: 1.0 g of 5-tert-butyloxycarbonyl-7-[2-(tert-butyldimethylsilyloxy)ethyl]-1,2,3,3a,5,9b-hexahydrocyclopenta[c]quinolin-4-one.

$^1$H-NMR (CDCl$_3$): 0.01 (s, 6H), 0.87 (s, 9H), 1.65 (s, 9H), 1.72 (m, 3H), 2.04 (m, 2H), 2.41 (m, 1H), 2.79 (t, 2H), 2.96 (td, 1H), 3.19 (q, 1H), 3.78 (t, 2H), 6.64 (d, 1H), 6.93 (dd, 1H), 7.14 (d, 1H).

4.3 ml (6.8 mmol) of n-butyllithium (1.6 M in hexane) is added in drops at –70° C. to a solution of 0.71 ml (6.8 mmol) of diethylamine in 50 ml of THF. After 1 hour at –70° C., a solution of 1.0 g (2.3 mmol) of 5-tert-butyloxycarbonyl-7-[2-(tert-butyldimethylsilyloxy)ethyl]-1,2,3,3a,5,9b-hexahydrocyclopenta[c]quinolin-4-one in 10 ml of THF is added to it. The batch is stirred for 1 hour at –70° C., then mixed with 2.87 g (9.1 mmol) of N-fluoro(phenylsulfonyl)imide and heated within 1 hour to room temperature. After 15 hours of stirring at room temperature, the reaction mixture is concentrated by evaporation and purified by column chromatography on silica gel with hexane-ethyl acetate: 0.77 g of product.

$^1$H-NMR (CDCl$_3$): 0.01 (s, 6H), 0.88 (s, 9H), 1.61–1.71 (m, 1H), 1.67 (s, 9H), 1.87–2.49 (m, 5H), 2.80 (t, 2H), 3.62 (dm, 1H), 3.81 (m, 2H), 6.68 (d, 1H), 7.00 (dd, 1H), 7.21 (d, 1H).

3a-Fluoro-7-(2-hydroxyethyl)-1,2,3,3a,5,9b-hexahydrocyclopenta[c]quinolin-4-one 0.77 g (1.7 mmol) of 5-tert-butyloxycarbonyl-7-[2-(tert-butyldimethylsilyloxy)ethyl]-3a-fluoro-1,2,3,3a,5,9b-hexahydrocyclopenta[c]quinolin-4-one is stirred in 10 ml of 4 M hydrochloric acidic dioxane for 2 hours at room temperature. The batch is concentrated by evaporation in a vacuum, the residue is taken up in ethyl acetate, washed with saturated NaHCO$_3$, dried (Na$_2$SO$_4$) and concentrated by evaporation in a vacuum. Column chromatography on silica gel with hexane-ethyl acetate yields 0.26 g of product.

MS (El) m/e=249 (M$^+$)

7-[2-{(N-tert-Butyloxycarbonyl)methylamino}ethyl]-3a-fluoro-1,2,3,3a,5,9b-hexahydrocyclopenta[c]quinolin-4-one A solution of 0.15 g (0.46 mmol) of 3a-fluoro-7-(2-hydroxyethyl)-1,2,3,3a,5,9b-hexahydrocyclopenta[c]quinolin-4-one in 20 ml of THF is mixed at –5° C. with 0.07 ml (0.5 mmol) of triethylamine and 0.04 ml (0.5 mmol) of methanesulfonyl chloride, and it is stirred for 1.5 hours at 0° C. The batch is acidified with 10% citric acid and extracted with ethyl acetate. The combined extracts are washed with water, dried (Na$_2$SO$_4$) and concentrated by evaporation in a vacuum. The residue is taken up in 20 ml of 2 M methanolic methylamine solution and refluxed for 4 hours. The volatile components are removed in a vacuum, and the residue is dissolved in 50 ml of dichloromethane. 0.31 g (1.4 mmol) of pyrocarbonic acid-di-tert-butyl ester is added to it, and after 4 hours, another 0.10 g is added to it. After 6 hours, the batch is diluted with dichloromethane, washed with water, dried (Na$_2$SO$_4$) and concentrated by evaporation in a vacuum. Column chromatography with hexane-ethyl acetate yields 0.12 g of product.

$^1$H-NMR (CDCl$_3$): 1.40 (s, 9H), 1.68 (m, 2H), 1.88–2.52 (m, 4H), 2.76 (t, 2H), 2.83 (s, 3H), 3.44 (t, 2H), 3.60 (dm, 1H), 6.66 (s, 1H), 6.90 (br., 1H), 7.17 (d, 1H), 8.31/8.57 (br., 1H).

7-[2-{(N-tert-Butyloxycarbonyl)methylamino}ethyl]-3a-fluoro-1,2,3,3a,5,9b-hexahydrocyclopenta[c]quinoline-4-thione A solution of 0.12 g (0.33 mmol) of 7-[2-{(N-tert-butyloxycarbonyl)methylamino}ethyl]-3a-fluoro-1,2,3,3a,5,9b-hexahydrocyclopenta[c]quinolin-4-one in 15 ml of THF is refluxed with 0.27 g (0.67 mmol) of Lawesson's reagent for 1.5 hours. Then, the reaction mixture is concentrated by evaporation, and the residue is purified by column chromatography on silica gel with hexane-ethyl acetate: 0.10 g of product.

$^1$H-NMR (CDCl$_3$): 1.41 (s, 9H), 1.67 (m, 2H), 1.88–2.59 (m, 4H), 2.76 (br.t, 2H), 2.84 (s, 3H), 3.44 (br.t, 2H), 3.50 (dm, 1H), 6.68 (br., 1H), 7.00 (br., 1H), 7.21 (d, 1H), 9.57 (br., 1H).

4-Amino-7-[2-{[N-tert-butyloxycarbonyl)methylamino}ethyl]-3a-fluoro-2,3,3a,5,9b-tetrahydro-1H-cyclopenta[c]quinoline 0.10 g (0.26 mmol) of 7-[2-{(N-tert-butyloxycarbonyl)methylamino)ethyl]-3a-fluoro-1,2,3,3a,5,9b-hexahydrocyclopenta[c]quinoline-4-thione is stirred in 10 ml of 7 M ammoniacal methanol for 2 hours at room temperature. After the volatile components are distilled off in a vacuum, the residue is purified by column chromatography on silica gel with dichloromethane-methanol: 89 mg of product.

¹H-NMR (CDCl₃): 1.43 (s, 9H), 1.56–2.50 (m, 6H), 2.75 (br.t, 2H), 2.83 (s, 3H), 3.42 (br.m, 2H), 3.48 (dd, 1H), 5.31 (s, 2H), 6.82 (br., 1H), 6.90 (s, 1H), 7.10 (d, 1H).

MS (FAB) m/e=362 (M⁺).

4-Amino-7-[2-(methylamino)ethyl]-3a-fluoro-2,3,3a, 5,9b-tetrahydro-1H-cyclopenta[c]quinoline dihydrochloride 85 mg (0.23 mmol) of 4-amino-7-[2-{(N-tert-butyloxycarbonyl)methylamino}methyl]-3a-fluoro-2,3,3a, 5,9b-tetrahydro-1H-cyclopenta[c]quinoline is stirred in 5 ml of 4 M hydrochloric acidic dioxane for 1 hour at room temperature. The volatile components are removed in a vacuum.

MS (Cl) m/e=262 ([MH−2 HCl]⁺).

EXAMPLE 7

4-Amino-7-[3-(3-chlorobenzylamino)propyl]-3a-fluoro-2,3,3a,9b-tetrahydro-1H-cyclopenta[c]quinoline dihydrochloride

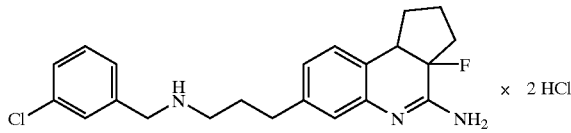

7-(2-Methoxycarbonylethenyl)-1,2,3,5-tetrahydrocyclo-penta[c]quinolin-4-one

A suspension of 528 mg (2.0 mmol) of 7-bromo-1,2,3,5-tetrahydrocyclopenta[c]quinolin-4-one (WO 99/41240), 0.36 ml (4.0 mmol) of acrylic acid methyl ester, 116 mg (0.1 mmol) of tetrakis(triphenylphosphine)palladium and 0.56 ml (4.0 mmol) of triethylamine in 25 ml of DMF is stirred for 3 hours at 120° C. The batch is diluted with ethyl acetate, washed with water, dried (Na₂SO₄) and concentrated by evaporation in a vacuum. Purification of the residue on silica gel with dichloromethane-ethanol yields 550 mg of product.

¹H-NMR ([D₆]-DMSO): δ=2.12 (pent, 2H), 2.80. (t, 2H), 3.12 (t, 2H), 3.77 (s, 3H), 6.61 (d, 1H), 7.52 (s, 1H), 7.56 (s, 2H), 7.67 (d, 1H), 11.19 (br.s, 1H).

7-(2-Methoxycarbonylethyl)-1,2,3,3a,5,9b-hexahydrocyclopenta[c]quinolin-4-one

A solution of 550 mg (2.0 mmol) of 7-(methoxycarbonylethenyl)-1,2,3,5-tetrahydrocyclopenta[c]quinolin-4-one in 130 ml of methanol-THF 3:1 is mixed with 972 mg (40.0 mmol) of magnesium and stirred for 24 hours at room temperature. The reaction mixture is filtered over glass fibers, the filter residue is washed with dichloromethane-methanol, and the combined filtrates are concentrated by evaporation in a vacuum. Purification of the residue on silica gel yields 120 mg of product.

¹H-NMR (CDCl₃): δ=1.57–1.77 (m, 3H), 2.02–2.18 (m, 2H), 2.31 (m, 1H), 2.63 (t, 2H), 2.91 (t, 2H), 2.94 (td, 1H), 3.23 (q, 1H), 3.69 (s, 3H), 6.58 (d, 1H), 6.84 (dd, 1H), 7.12 (d, 1H), 8.11 (br.s, 1H).

7-(3-Hydroxypropyl)-1,2,3,3a,5,9b-hexahydrocyclopenta[c]quinolin-4-one

A solution of 4.0 g (14.6 mmol) of 7-(2-methoxycarbonylethyl)-1,2,3,3a,5,9b-hexahydrocyclopenta[c]quinolin-4-one in 60 ml of THF and 100 ml of methanol is stirred for 24 hours with 29 ml of 1 M aqueous sodium hydroxide solution. The batch is set at pH 5 with 10% sulfuric acid and extracted with dichloromethane and ethyl acetate. The combined extracts are freeze-dried (Na₂SO₄) and concentrated by evaporation in a vacuum. After column chromatography on silica gel with dichloromethane-methanol, 3.4 g of 7-(carboxyethyl)-1,2,3, 3a,5,9b-hexahydrocyclopenta[c]quinolin-4-one is isolated.

¹H-NMR (CDCl₃, [D]₆-DMSO): δ=1.17–1.40 (m, 3H), 1.70 (m, 2H), 1.93 (m, 1H), 2.21 (t, 2H), 2.50 (m, 3H), 2.84 (q, 1H), 6.37 (d, 1H), 6.46 (dd, 1H), 6.73 (d, 1H), 9.27 (s, 1H). 3.1 g (11.9 mmol) of the acid is dissolved in 200 ml of THF and mixed at 0° C. with 1.23 ml (13.1 mmol) of ethyl chloroformate and 1.84 ml (13.1 mmol) of triethylamine. After 10 minutes, 2.25 g (59.5 mmol) of sodium borohydride is added to it, and 200 ml of methanol is added in drops within 10 minutes. After 30 minutes at room temperature, the batch is concentrated in a vacuum, and the residue is extracted with ethyl acetate-dichloromethane (9:1). The extracts are washed with saturated NaCl, dried (Na₂SO₄) and concentrated by evaporation in a vacuum. Column chromatography on silica gel with hexane-ethyl acetate yields 2.7 g of product.

¹H-NMR (CDCl₃): δ=1.58–1.79 (m, 4H), 1.89 (m, 2H); 2.10 (m, 2H), 2.30 (m, 1H), 2.67 (t, 2H), 2.94 (td, 1H), 3.23 (q, 1H), 3.70 (t, 2H), 6.60 (d, 1H), 6.87 (dd, 1H), 7.18 (d, 1H), 8.26 (br.s, 1H).

7-[3-(tert-Butyldimethylsilyloxy)propyl]-1,2,3,3a,5, 9b-hexahydrocyclopenta[c]-quinolin-4-one At 0° C., 3.65 g (24.5 mmol) of tert-butyldimethylsilyl-chloride and 3.29 g (48.9 mol) of imidazole are added to a solution of 3.0 g (12.2 mmol) of 7-(3-hydroxypropyl)-1,2, 3,3a,5,9b-hexahydrocyclopenta[c]quinolin-4-one in 50 ml of DMF. After 3 hours, the batch is diluted with ethyl acetate, washed with water, 10% citric acid and saturated NaHCO₃, dried (Na₂SO₄) and concentrated by evaporation in a vacuum. Column chromatography with hexane-ethyl acetate on silica gel yields 4.62 g of product.

¹H-NMR (CDCl₃): δ=0.05 (s, 6H), 0.91 (s, 9H), 1.54–1.84 (m, 3H), 2.00–2.14 (m, 2H), 2.28 (m, 1H), 2.61 (t, 2H), 2.92 (td, 1H), 3.21 (q, 1H), 3.62 (t, 2H), 6.53 (d, 1H), 6.82 (dd, 1H), 7.09 (d, 1H), 7.82 (br.s, 1H).

5-tert-Butyloxycarbonyl-7-[3-(tert-butyldimethylsilyloxy)propyl]-3a-fluoro-1,2,3,3a,5, 9b-hexahydrocyclopenta[c]quinolin-4-one A solution of 4.62 g (12.9 mmol) of 7-[3-(tert-butyldimethylsilyloxy)propyl]-1,2,3,3a,5,9b-hexahydrocyclopenta[c]quinolin-4-one in 250 ml of THF is stirred with 4.22 g (19.3 mmol) of pyrocarbonic acid-di-tert-butyl ester and 2.37 g (19.3 mmol) of 4-(dimethylamino)pyridine for 24 hours at room temperature. The solvent is removed in a vacuum, and the residue is purified by column chromatography on silica gel with hexane-ethyl acetate: 5.33 g of 5-tert-butyloxycarbonyl-7-[3-(tert-butyldimethylsilyloxy)propyl]-1,2,3,3a,5,9b-hexahydrocyclopenta[c]quinolin-4-one.

MS (El) m/e=459 (M⁺).

4.4 ml (2.2 mmol) of 0.5 M potassium hexamethyldisilazide-toluene solution is added in drops at −70° C. to 0.50 g (1.1 mmol) of 5-tert-butyloxycarbonyl-7-[3-(tert-butyldimethylsilyloxy)propyl]-1,2,3,3a,5,9b-hexahydrocyclopenta[c]quinolin-4-one in 20 ml of THF.

After 1 hour at −70° C., 0.95 g (3.3 mmol) of N-fluoro (phenylsulfonyl)imide is added to it and stirred for 4 hours at −70° C. and for 18 hours at room temperature. The batch is diluted with ethyl acetate, washed with water, dried ($Na_2SO_4$) and concentrated by evaporation in a vacuum. Column chromatography on silica gel with hexane-ethyl acetate yields 0.40 g of product.

$^1$H-NMR ($CDCl_3$): δ=0.06 (s, 6H), 0.91 (s, 9H), 1.62 (m, 2H), 1.65 (s, 9H), 1.81 (m, 2H), 1.87–2.45 (m, 4H), 2.64 (t, 2H), 3.59 (m, 1H), 3.63 (t, 2H), 6.66 (s, 1H), 6.97 (d, 1H), 7.18 (d, 1H).

3a-Fluoro-7-(3-hydroxypropyl)-1,2,3,3a,5,9b-hexahydrocyclopenta[c]quinolin-4-one 0.40 g (0.84 mmol) of 5-tert-butyloxycarbonyl-7-[3-(tert-butyldimethylsilyloxy)-propyl]-3a-fluoro-1,2,3,3a,5,9b-hexahydrocyclopenta[c]quinolin-4-one is dissolved in 5 ml of dichloromethane and treated with 5 ml of trifluoroacetic acid. After 1 hour at room temperature, the batch is diluted with ethyl acetate, washed with water and saturated $NaHCO_3$, dried ($Na_2SO_4$) and concentrated by evaporation in a vacuum. Column chromatography on silica gel with hexane-ethyl acetate yields 60 mg of product and 100 mg (0.28 mmol) of 3a-fluoro-7-(3-trifluorooxycarbonylpropyl)-1,2,3,3a,5,9b-hexahydrocyclopenta[c]quinolin-4-one, which is converted into another 60 mg of product with 192 mg (1.4 mmol) of potassium carbonate in 10 ml of MeOH.

$^1$H-NMR ($CDCl_3$): δ=1.60 (br., 1H), 1.72 (m, 2H), 1.91 (m, 2H), 1.95–2.52 (m, 4H), 2.67 (t, 2H), 3.60 (m, 1H), 3.71 (t, 2H), 6.69 (s, 1H), 6.92 (d, 1H), 7.16 (d, 1H), 8.63 (br.s, 1H).

7-[3-(3-Chlorobenzylamino)propyl]-3a-fluoro-1,2,3,3a,5,9b-hexahydrocyclopenta[c]quinolin-4-one A solution of 0.10 ml (1.4 mol) of DMSO in 5 ml of dichloromethane is added in drops at −70° C. to 0.08 ml (0.92 mmol) of oxalyl chloride in 10 ml of dichloromethane. After 10 minutes at −70° C., a solution of 120 mg (0.46 mmol) of 3a-fluoro-7-(3-hydroxypropyl)-3a-fluoro-1,2,3, 3a,5,9b-hexahydrocyclopenta[c]quinolin-4-one in 10 ml of dichloromethane is added, and after 2 hours at −70° C., 0.57 ml (4.1 mmol) of triethylamine is added. The batch is heated to room temperature, stirred for another hour and concentrated by evaporation in a vacuum. The residue is dissolved in 20 ml of 1,2-dichloroethane and 10 ml of THF, mixed with 0.06 ml (0.69 mmol) of 3-chlorobenzylamine, 145 mg (0.69 mmol) of sodium (tetracetoxy)borohydride and 0.27 ml (4.6 mmol) of acetic acid and stirred for 24 hours at room temperature. The batch is diluted with ethyl acetate, washed with water, dried ($Na_2SO_4$) and concentrated by evaporation in a vacuum. Column chromatography on silica gel with ethyl acetate-methanol yields 120 mg of product.

$^1$H-NMR ($CDCl_3$): δ=1.64 (m, 1H), 1.70–2.20 (m, 5H), 2.32 (m, 2H), 2.61 (m, 4H), 3.46 (br., 2H), 3.58 (dt, 1H), 3.80 (s, 2H), 6.80 (s, 1H), 6.90 (d, 1H), 7.24 (d, 1H), 7.33–7.43 (m, 3H), 7.48 (s, 1H), 10.53 (br.s, 1H).

7-[3-(N-tert-Butoxycarbonyl-3-chlorobenzylamino) propyl]-3a-fluoro-1,2,3,3a,5,9b-hexahydrocyclopenta[c]quinolin-4-one A solution of 120 mg (0.31 mmol) of 7-(3-(3-chlorobenzylamino)propyl]-3a-fluoro-1,2,3,3a,5,9b-hexahydrocyclopenta[c]quinolin-4-one in 20 ml of dichloromethane is mixed with 81 mg (0.37 mmol) of di-tert-butylcarboxylic acid anhydride and stirred for 24 hours at room temperature. The batch is diluted with dichloromethane, washed with water, dried ($Na_2SO_4$) and concentrated by evaporation in a vacuum. Column chromatography on silica gel with hexane-ethyl acetate yields 100 mg of product.

$^1$H-NMR ($CDCl_3$) δ=1.49 (s, 9H), 1.62–2.57 (m, 10H), 3.22 (br., 2H), 3.59 (dm, 1H), 4.41 (s, 2H), 6.54 (s, 1H), 6.86 (d, 1H), 7.10 (br., 1H), 7.14 (d, 1H), 7.21 (s, 1H), 7.25 (m, 2H), 7.59 (br., 1H).

7-[3-(N-tert-Butoxycarbonyl-3-chlorobenzylamino) propyl]-3a-fluoro-1,2,3,3a,5,9b-hexahydrocyclopenta[c]quinoline-4-thione A solution of 100 mg (0.21 mmol) of 7-[3-(N-tert-butoxycarbonyl-3-chlorobenzylamino)propyl]-3a-fluoro-1, 2,3,3a,5,9b-hexahydrocyclopenta[c]quinolin-4-one and 223 mg (0.55 mmol) of Lawesson's reagent in 15 ml of THF is refluxed for 1.5 hours. After concentration by evaporation in a vacuum, the residue is purified by column chromatography with hexane-ethyl acetate: 80 mg of product.

MS (Cl) m/e=503 ($M^+$).

4-Amino-7-[3-(N-tert-butoxycarbonyl-3-chlorobenzylamino)propyl]-3a-fluoro-2,3,3a,9b-tetrahydro-1H-cyclopenta[c]quinoline 80 mg (0.16 mmol) of 7-[3-(N-tert-butoxycarbonyl-3-chlorobenzylamino)propyl]-3a-fluoro-1,2,3,3a,5,9b-hexahydrocyclopenta[c]quinoline-4-thione is stirred in 15 ml of 7 M ammoniacal methanol for 1 hour at room temperature. After the volatile components are distilled off in a vacuum, the residue is purified by column chromatography on silica gel with dichloromethane-methanol: 60 mg of product.

MS (Cl) m/e=486 ($M^+$).

4-Amino-7-[3-(3-chlorobenzylamino)propyl]-3a-fluoro-2,3,3a,9b-tetrahydro-1H-cyclopenta[c] quinoline dihydrochloride 60 mg (0.12 mmol) of 4-amino-7-[3-(N-tert-butoxycarbonyl-3-chlorobenzylamino)-propyl]-3a-fluoro-2, 3,3a,9b-tetrahydro-1H-cyclopenta[c]quinoline is stirred in 5 ml of 4 M hydrochloric acidic dioxane for 1 hour at room temperature. The volatile components are removed in a vacuum: 70 mg.

MS (Cl) m/e=385 ([M-2 HCl]$^+$).

Produced analogously can be:
4-amino-3a,7-difluoro-2,3,3a,9b-tetrahydro-1H-cyclopenta [c]quinoline
4-amino-3a,8-difluoro-2,3,3a,9b-tetrahydro-1H-cyclopenta [c]quinoline
4-amino-3a-fluoro-7-methoxy-2,3,3a,9b-tetrahydro-1H-cyclopenta[c]quinoline
4-amino-3a-fluoro-8-methoxy-2,3,3a,9b-tetrahydro-1H-cyclopenta[c]quinoline
4-amino-3a-fluoro-7-methyl-2,3,3a,9b-tetrahydro-1H-cyclopenta[c]quinoline
4-amino-3a-fluoro-8-methyl-2,3,3a,9b-tetrahydro-1H-cyclopenta[c]quinoline
4-amino-3a-fluoro-8-nitro-2,3,3a,9b-tetrahydro-1H-cyclopenta[c]quinoline
4-amino-3a-fluoro-8-trifluoromethyl-2,3,3a,9b-tetrahydro-1H-cyclopenta[c]quinoline
4-amino-3a-fluoro-8-cyano-2,3,3a,9b-tetrahydro-1H-cyclopenta[c]quinoline
4-amino-3a-fluoro-7-(2-furanyl)-2,3,3a,9b-tetrahydro-1H-cyclopenta[c]quinoline 4-amino-7-(3-chlorobenzylamino)-3a-fluoro-1,2,3,3a,7,8,9,10b-octahydrodicyclopenta[c,g]quinoline dihydrochloride.

What is claimed is:

1. A compound of Formula 1, a tautomeric or isomeric form thereof or a salt thereof,

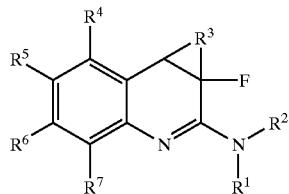

(I)

in which

R$^1$ and R$^2$, independently of one another, mean
 a) Hydrogen,
 b) C$_{1-6}$ alkyl,
 c) OR$^8$,
 d) NR$^8$R$^9$,
 e) CN,
 f) acyl,
 g) CO$_2$R$^{10}$,
 h) CONR$^8$R$^9$, or
 i) CSNR$^8$R$^9$, R$^3$ means:
 a saturated or unsaturated C$_{1-5}$ alkylene radical, which is optionally substituted in 1 to 4 places with OR$^8$, NR$^{11}$R$^{12}$ or, C$_{1-4}$ alkyl and in which 1 or 2 CH$_2$ groups are optionally replaced by carbonyl, and which is optionally bridged with a methano, ethano or propano group, R$^4$, R$^5$, R$^6$ and R$^7$, independently of one another, mean:
 a) Hydrogen,
 b) halogen,
 c) S(O)$_n$R$^8$,
 d) OR$^8$,
 e) COOR$^8$,
 f) COR$^8$,
 g) CONR$^8$R$^{13}$,
 h) CSNR$^8$R$^{13}$,
 i) C(NR$^8$)NR$^9$R$^{13}$,
 j) NR$^{14}$R$^{15}$,
 k) C$_{1-6}$ alkyl, which optionally is substituted with halogen, OR$^8$, SR$^8$, NR$^{14}$R$^{15}$, phenyl, 5- to 6-membered heteroaryl with 1–4 N, S or O atoms or C$_{3-7}$ cycloalkyl,
 l) C$_{3-7}$ cycloalkyl,
 m) C$_{2-6}$ alkenyl, optionally substituted with phenyl or halogen,
 n) C$_{2-6}$ alkinyl, optionally substituted with phenyl or halogen,
 o) C$_{6-10}$ aryl, which optionally is substituted with halogen, CN, C$_{1-4}$ alkyl, SR$^8$ or OR$^8$,
 p) 5- to 6-membered hetaryl with 1 to 4 N, O or S atoms, which contain a condensed benzene ring and is optionally substituted with halogen, NO$_2$, cyano, —OR$^8$, SR$^8$, C$_{1-4}$ alkyl, CF$_3$ or NR$^8$R$^{13}$,
 q) CN,
 r) NO$_2$,
 s) CF$_3$, or
 t) OCF$_3$, R$^4$ and R$^5$, R$^5$ and R$^6$, or R$^6$ and R$^7$ together with 2 adjacent carbon atoms form a 5- or 6-membered carbocycle, which is optionally substituted with NR$^{14}$R$^{15}$, R$^8$, R$^9$ and R$^{10}$, independently of one another, mean:
 a) Hydrogen,
 b) C$_{1-6}$ alkyl, or
 c) C$_{6-10}$ aryl, which optionally is substituted with halogen or C$_{1-4}$ alkyl, R$^{11}$ and R$^{12}$, independently of one another, mean
 a) Hydrogen,
 b) C$_{1-6}$ alkyl,
 b) COR$^{16}$,
 c) CO$_2$R$^{10}$,
 d) CONR$^8$R$^9$, or
 e) CSNR$^8$R$^9$, R$^{13}$ means:
 a) Hydrogen,
 b) C$_{1-6}$ alkyl, optionally substituted with halogens, amino, hydroxyl or sulfhydryl groups, or
 c) C$_{6-10}$ aryl, R$^{14}$ and R$^{15}$, independently of one another, mean:
 a) Hydrogen
 b) CO$_2$R$^{10}$, or
 c) C$_{1-6}$ alkyl, optionally substituted with halogen, hydroxy, C$_{1-4}$ alkoxy, nitro, amino, C$_{1-6}$ alkyl, trifluoromethyl, carboxyl, cyano, carboxamido, C$_{3-7}$ cycloalkyl, indanyl, 1,2,3,4-tetrahydronaphthyl, C$_{6-10}$ aryl, 5- or 6-membered heteroaryl with 1–4 nitrogen, oxygen or sulfur atoms, whereby the aryl and the heteroaryl radical is optionally substituted with halogen, hydroxy, C$_{1-4}$ alkoxy, C$_{1-4}$ alkyl, CF$_3$, NO$_2$, NH$_2$, N(C$_{1-4}$ alkyl)$_2$ or carboxyl, or R$^{14}$ and R$^{15}$ together with the nitrogen atom form a 5- to 7-membered saturated heterocycle, which optionally contains another oxygen, nitrogen or sulfur atom and optionally is substituted with C$_{1-4}$ alkyl, phenyl, benzyl or benzoyl or optionally has an unsaturated 5-membered heterocycle, optionally contains 1–3 N atoms and can be substituted with phenyl, C$_{1-4}$ halogen or CH$_2$—OH, R$^{16}$ means
 a) C$_{1-6}$ alkyl, or
 b) C$_{6-10}$ aryl, which optionally is substituted with halogen or C$_{1-4}$ alkyl, and n means 0, 1 or 2.

2. A compound according to claim 1, in which R$^1$ and R$^2$ mean hydrogen.

3. A compound according to claim 1, in which R$^3$ is C$_{1-5}$ alkylene.

4. A compound according to claim 1, in which R$^4$, R$^5$, R$^6$ and R$^7$ mean:
 a) Hydrogen,
 b) halogen,
 c) SR$^8$,
 d) OR$^8$,
 e) COOR$^8$,
 f) COR$^8$,
 g) CONR$^8$R$^{13}$,
 h) NR$^{14}$R$^{15}$,
 i) C$_{1-6}$ alkyl, which optionally is substituted with halogen, OR$^8$, SR$^8$, NR$^{14}$R$^{15}$, phenyl, 5- to 6-membered heteroaryl with 1–4 N, S or O atoms or C$_{3-7}$ cycloalkyl,
 j) phenyl, which optionally is substituted with halogen, CN, C$_{1-4}$ alkyl, SR$^8$ or OR$^8$,
 k) 5- to 6-membered heteroaryl with 1 to 4 N, O or S atoms, which contain a condensed benzene ring and can be substituted with halogen, NO$_2$, cyano, C$_{1-4}$ alkyl, CF$_3$ or NR$^8$R$^{13}$, l) CN,
m) $NO_2$,
n) $CF_3$,
o) $OCF_3$, or
p) $R^4$ and $R^5$, $R^5$ and $R^6$, or $R^6$ and $R^7$ together with 2 adjacent carbon atoms form a 5- or 6-membered carbocyclic compound, which can be substituted with $NR^{14}R^{15}$.

5. A compound according to claim 1,
4-Amino-3a-fluoro-2,3,3a,9b-tetrahydro-1H-cyclopenta[c]quinoline,
4-amino-3a,6-difluoro-2,3,3a,9b-tetrahydro-1H-cyclopenta[c]quinoline,
4-amino-8-bromo-3a-fluoro-2,3,3a,9b-tetrahydro-1H-cyclopenta[c]quinoline
4-amino-8-chloro-3a-fluoro-2,3,3a,9b-tetrahydro-1H-cyclopenta[c]quinoline,
4-amino-7-methylaminomethyl-3a-fluoro-2,3,3a,5,9b-tetrahydro-1H-cyclopenta[c]quinoline dihydrochloride,
4-amino-7-[2-(methylamino)ethyl]-3a-fluoro-2,3,3a,5,9b-tetrahydro-1H-cyclopenta[c]quinoline dihydrochloride,
4-amino-7-[3-(3-chlorobenzylamino)propyl]-3a-fluoro-2,3,3a,9b-tetrahydro-1H-cyclopenta[c]quinoline dihydrochloride.

6. A process for the production of compounds according to claim 1, wherein a compound of Formula (II) or its salt

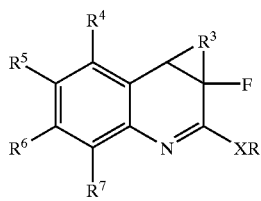

(IIa)

or

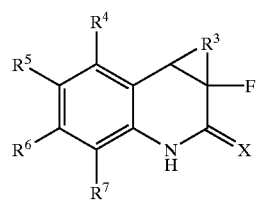

(IIb)

in which $R^3$ to $R^7$ have the meaning of claim 1, R is methyl or ethyl and X is oxygen or sulfur, is reacted with ammonia, primary or secondary amines, hydroxylamine and its derivatives or hydrazine and its derivatives, and optionally then the isomers are separated or the salts are formed.

7. A method for the treatment of a disease or condition which is triggered by a NOS synthase, comprising administering to a patient in need thereof a NOS synthase inhibitory amount of a compound according to claim 1.

8. A method of claim 7 wherein the disease or condition is a neurodegenerative disease or condition.

9. A compound of Formula IIb)

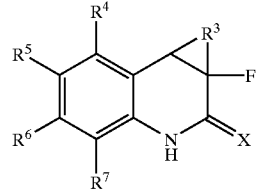

(IIb)

in which
$R^3$ means:
  a saturated or unsaturated $C_{1-5}$ alkylene radical, which is optionally substituted in 1 to 4 places with $OR^8$, $NR^{11}R^{12}$ or $C_{1-4}$ alkyl and in which 1 or, 2 $CH_2$ groups are optionally replaced by carbonyl, and which is optionally bridged with a methano, ethano or propano group,
$R^4$, $R^5$, $R^6$ and $R^7$, independently of one another, mean:
  a) Hydrogen,
  b) halogen,
  c) $S(O)_nR^8$,
  d) $OR^8$,
  e) $COOR^8$,
  f) $COR^8$,
  g) $CONR^8R^{13}$,
  h) $CSNR^8R^{13}$,
  i) $C(NR^8)NR^9R^{13}$,
  j) $NR^{14}R^{15}$,
  k) $C_{1-6}$ alkyl, which optionally is substituted with halogen, $OR^8$, $SR^8$, $NR^{14}R^{15}$, phenyl, 5- to 6-membered heteroaryl with 1–4 N, S or O atoms or $C_{3-7}$ cycloalkyl,
  l) $C_{3-7}$ cycloalkyl,
  m) $C_{2-6}$ alkenyl, optionally substituted with phenyl or halogen,
  n) $C_{2-6}$ alkinyl, optionally substituted with phenyl or halogen,
  o) $C_{6-10}$ aryl, which optionally is substituted with halogen, CN, $C_{1-4}$ alkyl, $SR^8$ or $OR^8$,
  p) 5- to 6-membered hetaryl with 1 to 4 N, O or S atoms, which contain a condensed benzene ring and is optionally substituted with halogen, $NO_2$, cyano, —$OR^8$, $SR^8$, $C_{1-4}$ alkyl, $CF_3$ or $NR^8R^{13}$,
  q) CN,
  r) $NO_2$,
  s) $CF_3$, or
  t) $OCF_3$,
$R^4$ and $R^5$, $R^5$ and $R^6$, or $R^6$ and $R^7$ together with 2 adjacent carbon atoms form a 5- or 6-membered carbocycle, which is optionally substituted with $NR^{14}R^{15}$,
$R^8$ and $R^9$, independently of one another, mean:
  a) Hydrogen,
  b) $C_{1-6}$ alkyl, or
  c) $C_{6-10}$ aryl, which optionally is substituted with halogen or $C_{1-4}$ alkyl,
$R^{11}$ and $R^{12}$, independently of one another, mean
  a) Hydrogen,
  b) $C_{1-6}$ alkyl,
  b) $COR^{16}$,
  c) $CO_2R^{10}$,
  d) $CONR^8R^9$, or
  e) $CSNR^8R^9$,
$R^{13}$ means:

a) Hydrogen,
b) $C_{1-6}$ alkyl, optionally substituted with halogens, amino, hydroxyl or sulfhydryl groups, or
c) $C_{6-10}$ aryl, $R^{14}$ and $R^{15}$, independently of one another, mean:
a) Hydrogen
b) $CO_2R^{10}$, or
c) $C_{1-6}$ alkyl, optionally substituted with halogen, hydroxy, $C_{1-4}$ alkoxy, nitro, amino, $C_{1-6}$ alkyl, trifluoromethyl, carboxyl, cyano, carboxamido, $C_{3-7}$ cycloalkyl, indanyl, 1,2,3,4-tetrahydronaphthyl, $C_{6-10}$ aryl, 5- or 6-membered heteroaryl with 1–4 nitrogen, oxygen or sulfur atoms, whereby the aryl and the heteroaryl radical is optionally substituted with halogen, hydroxy, $C_{1-4}$ alkoxy, $C_{1-4}$ alkyl, $CF_3$, $NO_2$, $NH_2$, $N(C_{1-4}$ alkyl$)_2$ or carboxyl, or $R^{14}$ and $R^{15}$ together with the nitrogen atom form a 5- to 7-membered saturated heterocycle, which optionally contains another oxygen, nitrogen or sulfur atom and optionally is substituted with $C_{1-4}$ alkyl, phenyl, benzyl or benzoyl or optionally has an unsaturated 5-membered heterocycle, optionally contains 1–3 N atoms and can be substituted with phenyl, $C_{1-4}$ halogen or $CH_2$—OH, and X is oxygen or sulfur.

10. A compound of Formula IVA

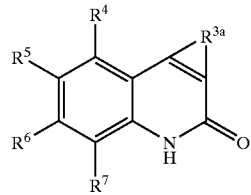

(IVa)

in which
$R^{3a}$ is —$(CH_2)_3$— and
$R^4$, $R^5$, $R^6$ and $R^7$, independently of one another, mean:
a) Hydrogen,
b) halogen,
c) $S(O)_nR^8$,
d) $OR^8$,
e) $COOR^8$,
f) $COR^8$,
g) $CONR^8R^{13}$,
h) $CSNR^8R^{13}$,
i) $C(NR^8)NR^9R^{13}$,
j) $NR^{14}R^{15}$,
k) $C_{1-6}$ alkyl, which optionally is substituted with halogen, $OR^8$, $SR^8$, $NR^{14}R^{15}$, phenyl, 5- to 6-membered heteroaryl with 1–4 N, S or O atoms or $C_{3-7}$ cycloalkyl,
l) $C_{3-7}$ cycloalkyl,
m) $C_{2-6}$ alkenyl, optionally substituted with phenyl or halogen,
n) $C_{2-6}$ alkinyl, optionally substituted with phenyl or halogen,
o) $C_{6-10}$ aryl, which optionally is substituted with halogen, CN, $C_{1-4}$ alkyl, $SR^8$ or $OR^8$,
p) 5- to 6-membered hetaryl with 1 to 4 N, O or S atoms, which contain a condensed benzene ring and is optionally substituted with halogen, $NO_2$, cyano, —$OR^8$, $SR^8$, $C_{1-4}$ alkyl, $CF_3$ or $NR^8R^{13}$,
q) CN,
r) $NO_2$,
s) $CF_3$, or
t) $OCF_3$, $R^4$ and $R^5$, $R^5$ and $R^6$, or $R^6$ and $R^7$ together with 2 adjacent carbon atoms form a 5- or 6-membered carbocycle, which is optionally substituted with $NR^{14}R^{15}$, $R^8$ and $R^9$, independently of one another, mean:
a) Hydrogen,
b) $C_{1-6}$ alkyl, or
c) $C_{6-10}$ aryl, which optionally is substituted with halogen or $C_{1-4}$ alkyl, $R^{13}$ means:
a) Hydrogen,
b) $C_{1-6}$ alkyl, optionally substituted with halogens, amino, hydroxyl or sulfhydryl groups, or
c) $C_{6-10}$ aryl, $R^{14}$ and $R^{15}$, independently of one another, mean:
a) Hydrogen
b) $CO_2R^{10}$, or
c) $C_{1-6}$ alkyl, optionally substituted with halogen, hydroxy, $C_{1-4}$ alkoxy, nitro, amino, $C_{1-6}$ alkyl, trifluoromethyl, carboxyl, cyano, carboxamido, $C_{3-7}$ cycloalkyl, indanyl, 1,2,3,4-tetrahydronaphthyl, $C_{6-10}$ aryl, 5- or 6-membered heteroaryl with 1–4 nitrogen, oxygen or sulfur atoms, whereby the aryl and the heteroaryl radical is optionally substituted with halogen, hydroxy, $C_{1-4}$ alkoxy, $C_{1-4}$ alkyl, $CF_3$, $NO_2$, $NH_2$, $N(C_{1-4}$ alkyl$)_2$ or carboxyl, or $R^{14}$ and $R^{15}$ together with the nitrogen atom form a 5- to 7-membered saturated heterocycle, which optionally contains another oxygen, nitrogen or sulfur atom and optionally is substituted with $C_{1-4}$ alkyl, phenyl, benzyl or benzoyl or optionally has an unsaturated 5-membered heterocycle, optionally contains 1–3 N atoms and can be substituted with phenyl, $C_{1-4}$ halogen or $CH_2$—OH, whereby $R^4$–$R^7$ do not simultaneously mean hydrogen.

11. A method of claim 7 wherein the disease or condition is an inflammatory disease or condition.

12. A method of claim 7 wherein the disease or condition is an auto-immune disorder or condition.

13. A method of claim 7 wherein the disease or condition is a cardiovascular disease or condition.

14. A pharmaceutical composition comprising a compound of claim 1, and a pharmaceutically acceptable excipient.

* * * * *